(12) United States Patent
Aikawa

(10) Patent No.: US 11,320,382 B2
(45) Date of Patent: May 3, 2022

(54) COMPONENT MEASUREMENT DEVICE, COMPONENT MEASUREMENT METHOD, AND COMPONENT MEASUREMENT PROGRAM

(71) Applicant: TERUMO KABUSHIKI KAISHA, Tokyo (JP)

(72) Inventor: Ryokei Aikawa, Hiratsuka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 542 days.

(21) Appl. No.: 16/115,682

(22) Filed: Aug. 29, 2018

(65) Prior Publication Data
US 2019/0011371 A1    Jan. 10, 2019

Related U.S. Application Data

(63) Continuation of application No. PCT/JP2016/084049, filed on Nov. 17, 2016.

(30) Foreign Application Priority Data

Mar. 8, 2016    (JP) .............................. JP2016-044694

(51) Int. Cl.
| | | |
|---|---|---|
| *G01N 21/78* | (2006.01) | |
| *G01N 33/66* | (2006.01) | |
| *G01N 33/72* | (2006.01) | |
| *G01N 21/31* | (2006.01) | |

(52) U.S. Cl.
CPC .............. *G01N 21/78* (2013.01); *G01N 21/31* (2013.01); *G01N 33/66* (2013.01); *G01N 33/72* (2013.01); *G01N 33/721* (2013.01)

(58) Field of Classification Search
CPC ........ G01N 21/78; G01N 33/66; G01N 33/72; G01N 21/31; G01N 33/721; G01N 21/314; G01N 2021/3148; G01N 2021/314

See application file for complete search history.

(56) References Cited

U.S. PATENT DOCUMENTS

2005/0171415 A1    8/2005 Hirao

FOREIGN PATENT DOCUMENTS

| | | |
|---|---|---|
| CN | 1653324 A | 8/2005 |
| EP | 1 037 048 A | 9/2000 |
| EP | 1 491 134 A | 12/2004 |

(Continued)

OTHER PUBLICATIONS

Translation of the Written Opinion dated Feb. 21, 2017 in corresponding PCT application No. PCT/JP2016/084049.

(Continued)

*Primary Examiner* — Samuel P Siefke
(74) *Attorney, Agent, or Firm* — Foley & Lardner LLP

(57) ABSTRACT

A component measurement device for measuring a component of interest in blood based on an optical property of a mixture containing a pigmentary component colored by a color reaction between the component of interest in the blood and a reagent, the component measurement device including: an absorbance obtaining unit configured to obtain a measured value of absorbance of the mixture at a measuring wavelength; and an absorbance correction unit configured to correct the measured value of absorbance of the mixture at the measuring wavelength based on information on scattered light and a ratio between reduced hemoglobin and oxygenated hemoglobin in erythrocytes.

16 Claims, 16 Drawing Sheets

(56) References Cited

FOREIGN PATENT DOCUMENTS

| | | |
|---|---|---|
| EP | 1 978 361 A | 10/2008 |
| JP | H07-34758 B2 | 4/1995 |
| JP | 2002-306458 A | 10/2002 |
| JP | 2014-233344 A | 12/2014 |
| WO | WO-2006/065898 A | 6/2006 |
| WO | WO-2015/137074 A1 | 9/2015 |

OTHER PUBLICATIONS

Extended European Search Report dated Sep. 18, 2019 for corresponding Application No. 16893594.8 (7 pages).
International Search Report with English language translation and Written Opinion issued in International Application No. PCT/JP2016/084049 dated Feb. 21, 2017.
Office Action dated Oct. 10, 2020 in corresponding Chinese Application No. 201680075916.0.

COMPONENT MEASUREMENT DEVICE, COMPONENT MEASUREMENT METHOD, AND COMPONENT MEASUREMENT PROGRAM

CROSS-REFERENCE TO RELATED APPLICATIONS

This is a bypass continuation of PCT Application No. PCT/JP2016/084049 filed on Nov. 17, 2016, which claims priority to Japanese Application No. 2016-044694, filed on Mar. 8, 2016. The contents of these applications are hereby incorporated by reference in their entireties.

BACKGROUND

The present disclosure relates to a component measurement device, a component measurement method, and a component measurement program. Particularly, the present disclosure relates to a component measurement device, a component measurement method, and a component measurement program for measuring a component of interest in blood.

BACKGROUND ART

In the biochemical field and the medical field, conventionally, the following technique has been known as a method for measuring a target component (also referred to as a "component of interest") contained in blood (whole blood) or a sample. That is, blood is separated into a part containing a component of interest and a part without the component of interest so as to measure an amount or a concentration of the component of interest. For example, in a known technique for measuring a glucose concentration (mg/dL) in plasma, a plasma component is separated from blood with a filter or the like so as to measure the glucose concentration in plasma.

However, it is difficult to thoroughly separate the plasma component in the blood in a short time. In addition, due to variations in the performance of the filter or the like used for the separation, a hemocyte component may be partially contained in the separated plasma component so that it is difficult to measure the glucose concentration precisely. Further, there is known a method for measuring a glucose concentration after hemolysis of blood, as disclosed in JP H07-34758 B. However, as this is similar to plasma separation, it takes time to hemolyze the blood, and a hemocyte component may remain in a liquid after the hemolysis.

On the other hand, whole blood measurement by absorption photometry is known as one method for measuring a component of interest in blood without separation of the component of interest from the blood and without hemolysis of the blood. According to this method, the time required for measuring the component of interest is reduced, as compared with the method involving the step of separating the component of interest and the step of hemolysis. However, when another component different from the component of interest is contained in the blood, the other component may cause optical phenomena such as light absorption and light scattering and may act as a disturbance factor in measurement. In order to maintain accuracy in measuring the component of interest, it is required to eliminate effects of this disturbance factor. In order to eliminate effects of a disturbance factor, various methods have been proposed.

WO 2015/137074 A discloses a component measurement device and a component measurement method in which an effect level of a disturbance factor at a measuring wavelength is estimated from a measured value in a long wavelength band longer than the measuring wavelength, and a measured value at the measuring wavelength is corrected based on the estimated effect level of the disturbance factor, and the measured value at the measuring wavelength is further corrected based on a predicted hematocrit level, whereby a glucose concentration in a plasma component can be measured.

SUMMARY

According to the component measurement device and the component measurement method disclosed in WO 2015/137074 A, a glucose concentration in a plasma component is measured from blood with high accuracy without separation of the plasma component containing glucose, a component of interest, from the blood. However, there is still room for improvement in estimation accuracy of an effect level of a disturbance factor such as light scattering due to a hemocyte component and the like in the blood, and light absorption due to hemoglobin in the blood.

An object of certain embodiments of the present invention is to provide a component measurement device, a component measurement method, and a component measurement program capable of measuring a predetermined component of interest with high accuracy without separating the predetermined component of interest from blood.

According to one embodiment, a component measurement device is for measuring a component of interest in blood based on an optical property of a mixture containing a pigmentary component colored by a color reaction between the component of interest in the blood and a reagent. The component measurement device is configured to correct a measured value of absorbance of the mixture at a measuring wavelength based on information on scattered light and a ratio between reduced hemoglobin and oxygenated hemoglobin in erythrocytes.

According to one aspect, the component measurement device includes: an absorbance obtaining unit configured to obtain a first measured value and a second measured value which are the absorbance of the mixture at a first wavelength and the absorbance of the mixture at a second wavelength both of which are within a long wavelength band longer than the measuring wavelength within a wavelength band corresponding to the full width at half maximum of a peak wavelength band in an absorbance spectrum of the pigmentary component, a third measured value and a fourth measured value which are the absorbance of the mixture at a third wavelength and the absorbance of the mixture at a fourth wavelength both of which are within a wavelength band shorter than the measuring wavelength within a wavelength band corresponding to the full width at half maximum, and a fifth measured value which is the absorbance of the mixture at the measuring wavelength; an absorbance correction unit configured to correct the fifth measured value, using the first measured value to the fourth measured value, wherein, the third wavelength is a wavelength at which a difference in an absorption coefficient between the reduced hemoglobin and the oxygenated hemoglobin is equal to or less than a first predetermined value, and the fourth wavelength is a wavelength at which said difference in the absorption coefficient is more than the first predetermined value.

In one aspect, the third wavelength is a wavelength at which a ratio of the absorption coefficient of the oxygenated hemoglobin to the absorption coefficient of the reduced hemoglobin is equal to or more than a first predetermined threshold, and the fourth wavelength is a wavelength at which the ratio of the absorption coefficient of the oxygenated hemoglobin to the absorption coefficient of the reduced hemoglobin is less than the first predetermined threshold.

In one aspect, the third wavelength is a wavelength at which the absorption coefficient of the reduced hemoglobin and the absorption coefficient of the oxygenated hemoglobin are equal. In other words, the third wavelength is a wavelength at which the ratio of the absorption coefficient of the oxygenated hemoglobin to the absorption coefficient of the reduced hemoglobin becomes 1.

In one aspect, the third wavelength is in a range from 520 nm to 550 nm or 565 nm to 585 nm.

In one aspect, the fourth wavelength is preferably more than 550 nm and less than 565 nm or more than 585 nm and less than 600 nm.

In one aspect, the first wavelength is a wavelength at which a difference in an absorption coefficient between the reduced hemoglobin and the oxygenated hemoglobin is equal to or less than a second predetermined value, and the second wavelength is a wavelength at which said difference is larger than the second predetermined value.

In one aspect, the first wavelength is a wavelength at which the ratio of the absorption coefficient of the oxygenated hemoglobin to the absorption coefficient of the reduced hemoglobin is equal to or more than the first threshold and equal to or less than a second threshold, and as the second wavelength, a wavelength at which the ratio of the absorption coefficient of the oxygenated hemoglobin to the absorption coefficient of the reduced hemoglobin is less than the first threshold or more than the second threshold.

In one aspect, the first wavelength is a wavelength at which the absorption coefficient of the reduced hemoglobin and the absorption coefficient of the oxygenated hemoglobin are equal.

In one aspect, the first wavelength is in a range from 790 nm to 810 nm.

In one aspect, the second wavelength is a wavelength at which an absorbance of the pigmentary component is 10% or less of an absorbance of the pigmentary component at the measuring wavelength.

In one aspect, the second wavelength is a wavelength at which the absorbance of the pigmentary component is 0% of the absorbance of the pigmentary component at the measuring wavelength.

In one aspect, the measuring wavelength is 600 nm or more and 700 nm or less.

According to a second embodiment, a component measurement method is for measuring a component of interest in blood based on an optical property of a mixture containing a pigmentary component colored by a color reaction between the component of interest in the blood and a reagent. The component measurement method comprises correcting a measured value of absorbance of the mixture at a measuring wavelength based on information on scattered light and a ratio between reduced hemoglobin and oxygenated hemoglobin in erythrocytes.

According to a third embodiment, a component measurement program is for measuring a component of interest in blood based on an optical property of a mixture containing a pigmentary component colored by a color reaction between the component of interest in the blood and a reagent. The component measurement program causes a component measurement device to correct a measured value of absorbance of the mixture at a measuring wavelength based on information on scattered light and a ratio between reduced hemoglobin and oxygenated hemoglobin in erythrocytes.

According to certain embodiments described in this disclosure, it is possible to provide a component measurement device, a component measurement method, and a component measurement program capable of measuring a predetermined component of interest with high accuracy without separating the predetermined component of interest from blood.

DETAILED DESCRIPTION

Figure 1:
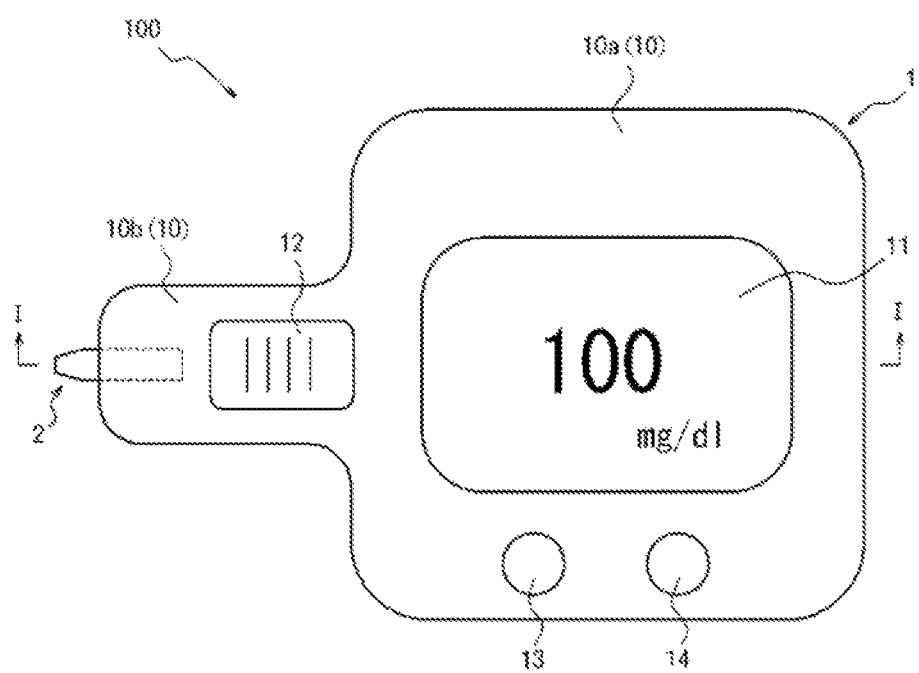
FIG. 1 is a top view of a component measurement device set in which a component measurement chip is attached to a component measurement device according to an embodiment of the present invention.

Hereinafter, embodiments of a component measurement device, a component measurement method, and a component measurement program will be described with reference to FIGS. 1 to 16. In the drawings, the same members are denoted with the same reference numerals.

Figure 2:
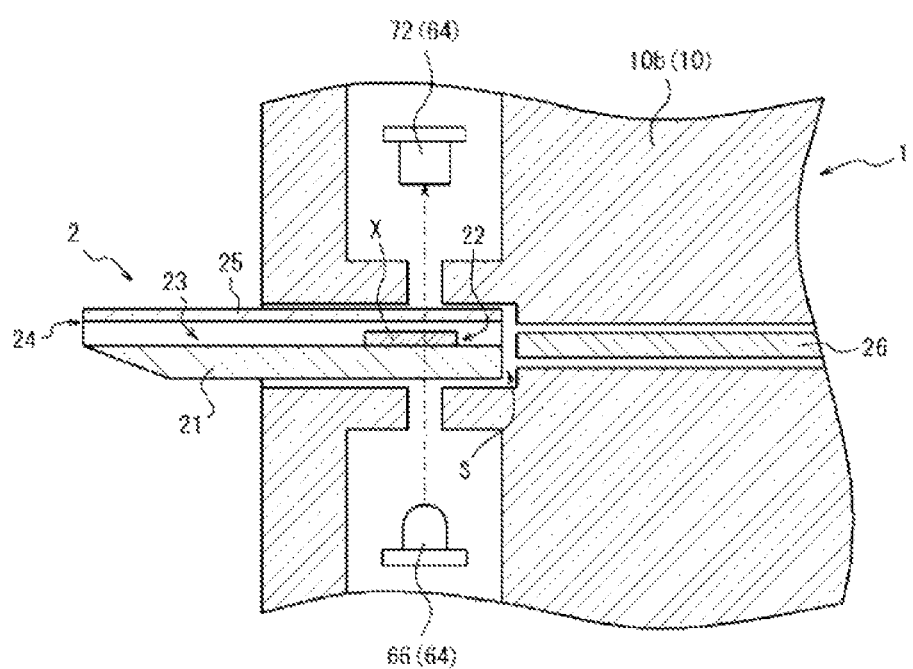
FIG. 2 is an enlarged cross-sectional view of a cross-sectional view taken along line I-I of FIG. 1, illustrating the vicinity of a portion where the component measurement chip is attached.

First, an embodiment of a component measurement device will be described. FIG. 1 is a top view of a component measurement device set 100 in which a component measurement chip 2 is attached to a component measurement device 1 according to this embodiment. FIG. 2 is an enlarged cross-sectional view of a cross-sectional view taken along line I-I of FIG. 1, illustrating the vicinity of a portion where the component measurement chip 2 is attached.

The component measurement device set 100 includes the component measurement device 1 and the component measurement chip 2. The component measurement device 1 of this embodiment is a blood glucose level measurement device capable of measuring a glucose concentration (mg/dL) in a plasma component, a component of interest, in blood. The component measurement chip 2 of this embodiment is a blood glucose level measurement chip that is attachable to a tip of the blood glucose level measurement device, or the component measurement device 1. It should be noted that the term "blood" herein represents whole blood that includes all components, not blood that has been separated into components.

The component measurement device 1 is provided with a housing 10 including a resin material; a display unit 11 including a button group provided on an upper surface of the housing 10, and a liquid crystal or light emitting diode (LED) and the like provided on the upper surface of the housing 10; and a detachment lever 12 that is handled when the component measurement chip 2 attached to the component measurement device 1 is detached. The button group of this embodiment includes a power button 13, and an operation button 14.

The housing 10 includes a main body 10a having a substantially rectangular outline as viewed from the top, being provided with the button group and the display unit 11 on the upper surface (see FIG. 1); and a chip attaching portion 10b protruding outward from the main body 10a, being provided with the detachment lever 12 on the upper surface (see FIG. 1). As illustrated in FIG. 2, the inside of the chip attaching portion 10b is partitioned to form a chip attaching space S that has one end at a tip opening formed on a surface of a tip of the chip attaching portion 10b. When the component measurement chip 2 is attached to the component measurement device 1, the component measurement chip 2 is inserted into the chip attaching space S from the outside through the tip opening, and the component measurement chip 2 is pushed to a predetermined position, so that the chip attaching portion 10b of the component measurement device 1 is locked in the component measurement chip 2. Accordingly, the component measurement chip 2 can be attached to the component measurement device 1. It should be noted that the component measurement chip 2 may be locked in the component measurement device 1 by various configurations. For example, a claw engageable with a part of the component measurement chip 2 may be provided inside the chip attaching portion 10b.

Conversely, when the component measurement chip 2 attached to the component measurement device 1 is detached from the component measurement device 1, the detachment lever 12 is handled from the outside of the housing 10 to release the lock between the component measurement chip 2 and the chip attaching portion 10b of the component measurement device 1. In conjunction with the release of the lock, an ejector pin 26 (see FIG. 2) inside the housing 10 moves so that the component measurement chip 2 is detached from the component measurement device 1.

The housing 10 of this embodiment is provided with the main body 10a having a substantially rectangular shape as viewed from the top (see FIG. 1), and the chip attaching portion 10b protruding outward from the main body 10a. However, it should be noted that the housing 10 is not limited to the shape of this embodiment as long as it includes a chip attaching portion to which the component measurement chip 2 is attachable. Therefore, besides the shape of the housing 10 of this embodiment, various shapes that enable a user to grasp the housing 10 with one hand are also employable.

The display unit 11 displays information on the component of interest measured by the component measurement device 1. In this embodiment, the glucose concentration (mg/dL) measured by the blood glucose level measurement device, or the component measurement device 1, is displayed on the display unit 11. It should be noted that the display unit 11 may display not only the information on the component of interest but also various kinds of information such as measurement conditions of the component measurement device 1 and instruction information instructing a user to do a predetermined operation. While checking the contents displayed on the display unit 11, the user can handle the power button 13 and the operation button 14 of the button group.

Figure 3:
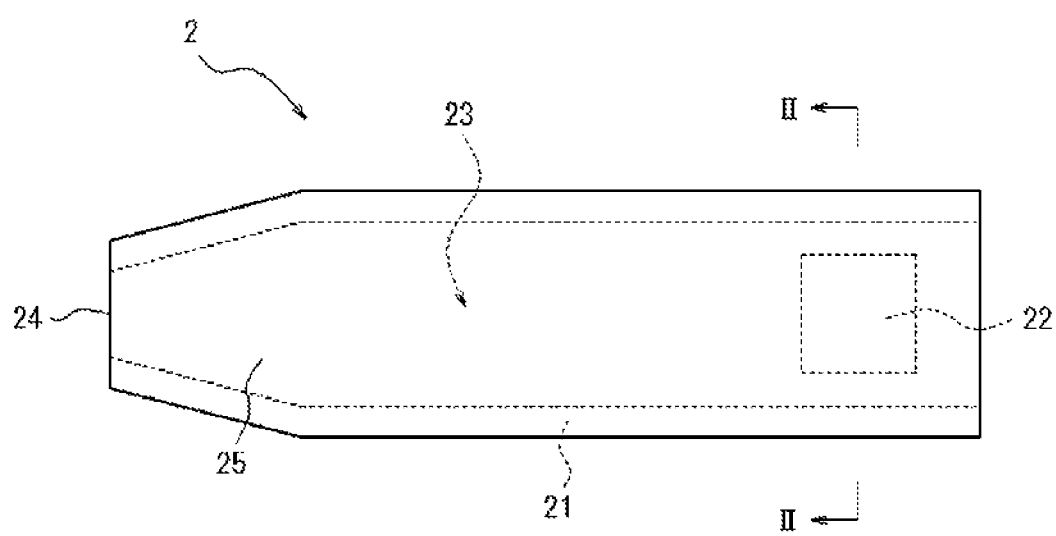
FIG. 3 is a top view of the component measurement chip illustrated in FIG. 1.
Figure 4:
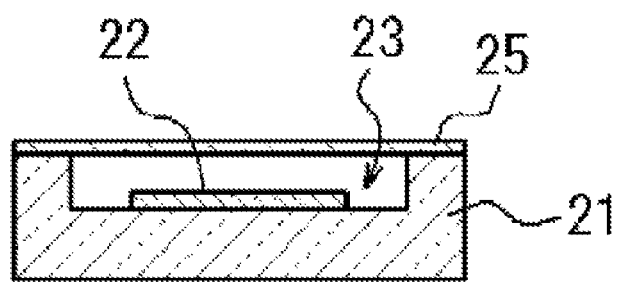
FIG. 4 is a cross-sectional view taken along line II-II of FIG. 3.

Next, the component measurement chip 2 single body will be described. FIG. 3 is a top view of the component measurement chip 2. FIG. 4 is a cross-sectional view taken along line II-II of FIG. 3. As illustrated in FIG. 3 and FIG. 4, the component measurement chip 2 includes a base member 21 having a substantially rectangular plate-like outline, a coloring reagent 22 as a reagent held by the base member 21, and a cover member 25 that covers the base member 21.

An external surface of the base member 21 on one side in a thickness direction is formed with a groove. The groove of the base member 21 is covered by the cover member 25 so as to form a hollow portion extending in a direction perpendicular to the thickness direction. This hollow portion forms a flow path 23 of the component measurement chip 2. One end of the flow path 23 is formed with a supply unit 24 capable of supplying blood from the outside. In an inner wall of the flow path 23, the bottom of the groove of the base member 21 holds the coloring reagent 22. The blood supplied from the outside to the supply unit 24 flows along the flow path 23, utilizing, for example, a capillary action. Reaching the position where the coloring reagent 22 is held, the blood contacts with the coloring reagent 22 and undergoes a color reaction so that a pigmentary component is colored.

Although the flow path 23 of this embodiment includes the hollow portion partitioned by the base member 21 and the cover member 25, the flow path is not limited to this configuration. A flow path may be formed simply by a groove formed on the external surface of the base member 21 on one side in the thickness direction.

In regard to materials of the base member 21 and the cover member 25, transparent materials are preferably used from a viewpoint of transmission of light. Examples of the transparent materials include transparent organic resin materials such as polyethylene terephthalate (PET), polymethyl methacrylate (PMMA), polystyrene (PS), cyclic polyolefin (COP), cyclic olefin copolymer (COC), and polycarbonate (PC); and transparent inorganic resin materials such as glass and quartz.

The coloring reagent 22 as a reagent reacts with the component of interest in the blood and causes a color reaction to color the component of interest depending on concentrations of the component of interest in the blood. The coloring reagent 22 of this embodiment is applied to the bottom of the groove serving as the flow path 23. The coloring reagent 22 of this embodiment reacts with glucose, the component of interest, in the blood. Examples of the coloring reagent 22 of this embodiment include a mixed reagent of (i) glucose oxidase (GOD), (ii) peroxidase (POD), (iii) 1-(4-sulfophenyl)-2,3-dimethyl-4-amino-5-pyrazolone, and (iv) N-ethyl-N-(2-hydroxy-3-sulfopropyl)-3,5-dimethylaniline, sodium salt, monohydrate (MAOS); and a mixed reagent of glucose dehydrogenase (GDH), a tetrazolium salt, and an electron mediator. A buffering agent such as a phosphate buffer solution may also be contained in the coloring reagent 22. It should be noted that types and components of the coloring reagent 22 are not limited to these examples.

As the coloring reagent 22 in this embodiment, used is a reagent in which a peak wavelength of an absorbance spectrum of the pigmentary component colored by the color reaction between the blood glucose and the coloring reagent 22 differs from a peak wavelength attributed to light absorption characteristics of hemoglobin in hemocytes. In the coloring reagent 22 of this embodiment, the peak wavelength in the absorbance spectrum of the pigmentary component colored by the color reaction between the blood glucose and the coloring reagent 22 is around 650 nm, but the coloring reagent 22 is not limited to one having a peak wavelength around 650 nm. The details will be described later.

When measuring the component of interest with the component measurement device 1, the component measurement chip 2 is attached to the inside of the chip attaching portion 10b as illustrated in FIG. 2. When blood is supplied to the supply unit 24 provided at one end of the component measurement chip 2, the blood flows along the flow path 23 by, for example, a capillary action. Reaching the position where the coloring reagent 22 in the flow path 23 is held, the blood reacts with the coloring reagent 22 at this position. The component measurement device 1 of what is called colorimetric type emits light toward the position where the coloring reagent 22 is held, detects an amount of transmitted light (or an amount of reflected light), and obtains a detection signal that correlates with the intensity of coloring depending on concentrations in the blood. Then, the component measurement device 1 measures the component of interest by reference to a calibration curve prepared in advance. It should be noted that the component measurement device 1 of this embodiment is configured to measure a glucose concentration (mg/dL) in a plasma component of blood.

Figure 5:
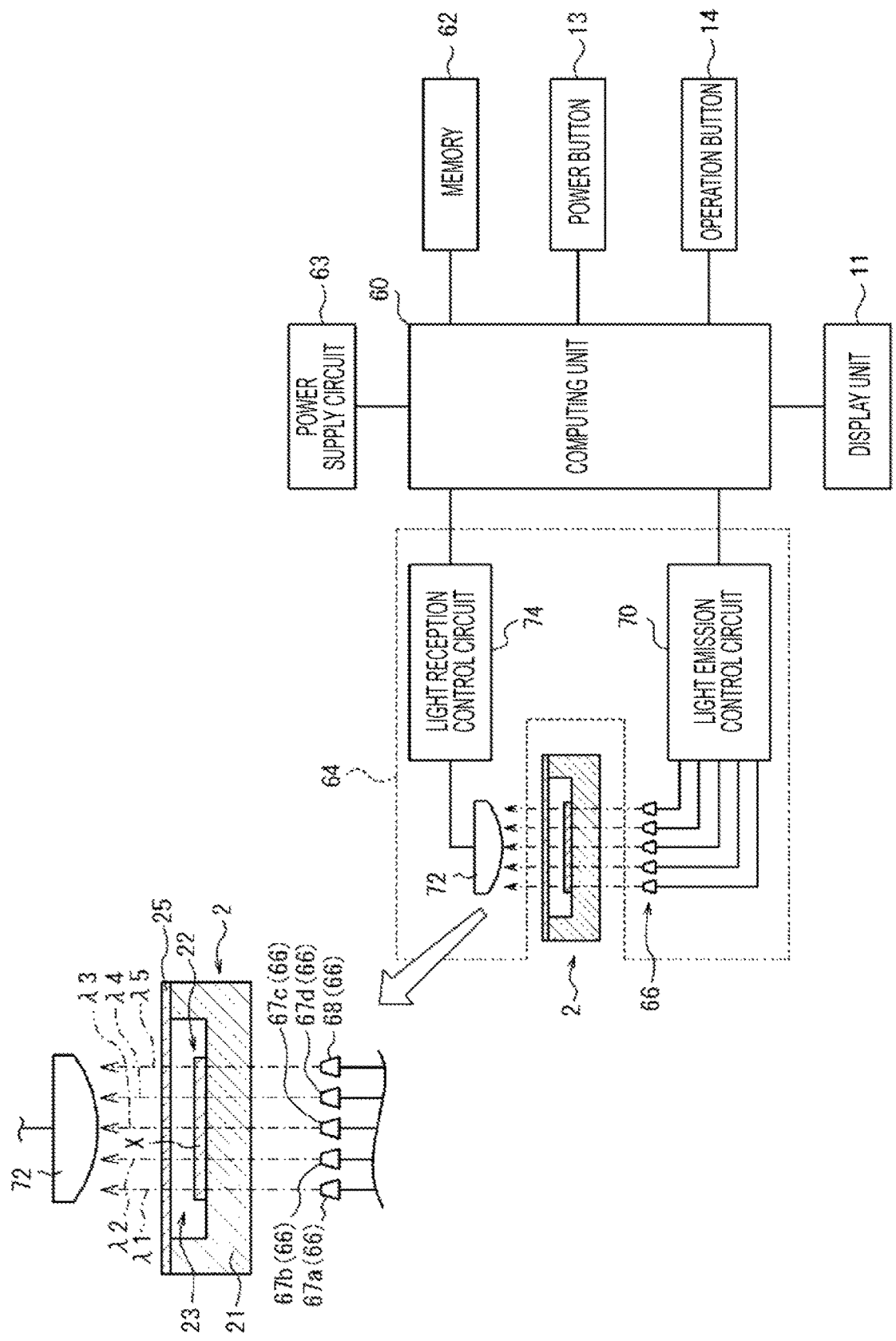
FIG. 5 is an electric block diagram of the component measurement device illustrated in FIG. 1.

FIG. 5 is an electric block diagram of the component measurement device 1 illustrated in FIGS. 1 and 2. For convenience sake, FIG. 5 also illustrates a cross section (the same cross section as FIG. 4) of the component measurement chip 2 attached to the component measurement device 1. FIG. 5 separately illustrates an enlarged view of the vicinity of the component measurement chip 2 on the upper left. Hereinafter, the component measurement device 1 will be described in more detail.

As illustrated in FIG. 5, in addition to the housing 10, the display unit 11, the detachment lever 12, the power button 13, and the operation button 14, the component measurement device 1 includes a computing unit 60, a memory 62, a power supply circuit 63, and a measurement optical system 64.

The computing unit 60 includes a micro-processing unit (MPU) or a central processing unit (CPU). Reading and executing a program stored in the memory 62 or the like, the computing unit 60 can control each unit. The memory 62 includes a volatile or involatile non-transitory storage medium and is configured to read or write various data (including programs) necessary for carrying out the component measurement method described herein. In accordance with operations of the power button 13, the power supply circuit 63 supplies power to each unit in the component measurement device 1 including the computing unit 60 or stops supplying the power.

The measurement optical system 64 is an optical system capable of obtaining optical properties of a mixture X containing the pigmentary component colored by the color reaction between the blood and the coloring reagent 22 as a reagent. The measurement optical system 64 specifically includes a light emitting unit 66, a light emission control circuit 70, a light receiving unit 72, and a light reception control circuit 74.

The light emitting unit 66 of this embodiment includes five types of light sources 67a, 67b, 67c, 67d, and 68. The light sources 67a to 67d and 68 emit light having different spectral-radiance characteristics (such as visible light and infrared light). Hereinafter, for convenience sake, the light source 67a, the light source 67b, the light source 67c, the light source 67d, the light source 68 are referred to as a "first light source 67a", a "second light source 67b", a "third light source 67c", a "fourth light source 67d", and a "fifth light source 68", respectively.

The first to fifth light sources 67a, 67b, 67c, 67d, and 68 have different emission wavelengths: first to fifth wavelengths $\lambda 1$, $\lambda 2$, $\lambda 3$, $\lambda 4$, and $\lambda 5$. Usable examples of the different types of light sources 67a to 67d and 68 include various types of light-emitting elements such as an LED, an organic electro-luminescence (EL), an inorganic EL, and a laser diode (LD).

As illustrated in FIGS. 2 and 5, the light receiving unit 72 of this embodiment includes one light receiving element opposed to the light emitting unit 66 across the component measurement chip 2. The light receiving unit 72 receives transmitted light that is emitted from the first to fifth light sources 67a to 67d and 68 of the light emitting unit 66 to the position where the coloring reagent 22 is held in the component measurement chip 2 and that is transmitted through the component measurement chip 2. Usable examples of the light receiving unit 72 include various types of photoelectric conversion elements such as a photo diode (PD), a photo conductor, and a photo transistor.

The light emission control circuit 70 supplies drive power signals to the first to fifth light sources 67a to 67d and 68 so as to turn on or off the first to fifth light sources 67a to 67d and 68. The light reception control circuit 74 obtains digital signals (hereinafter referred to as "detection signals") by logarithmic conversion and A/D conversion of analog signals output from the light receiving unit 72.

Figure 6:
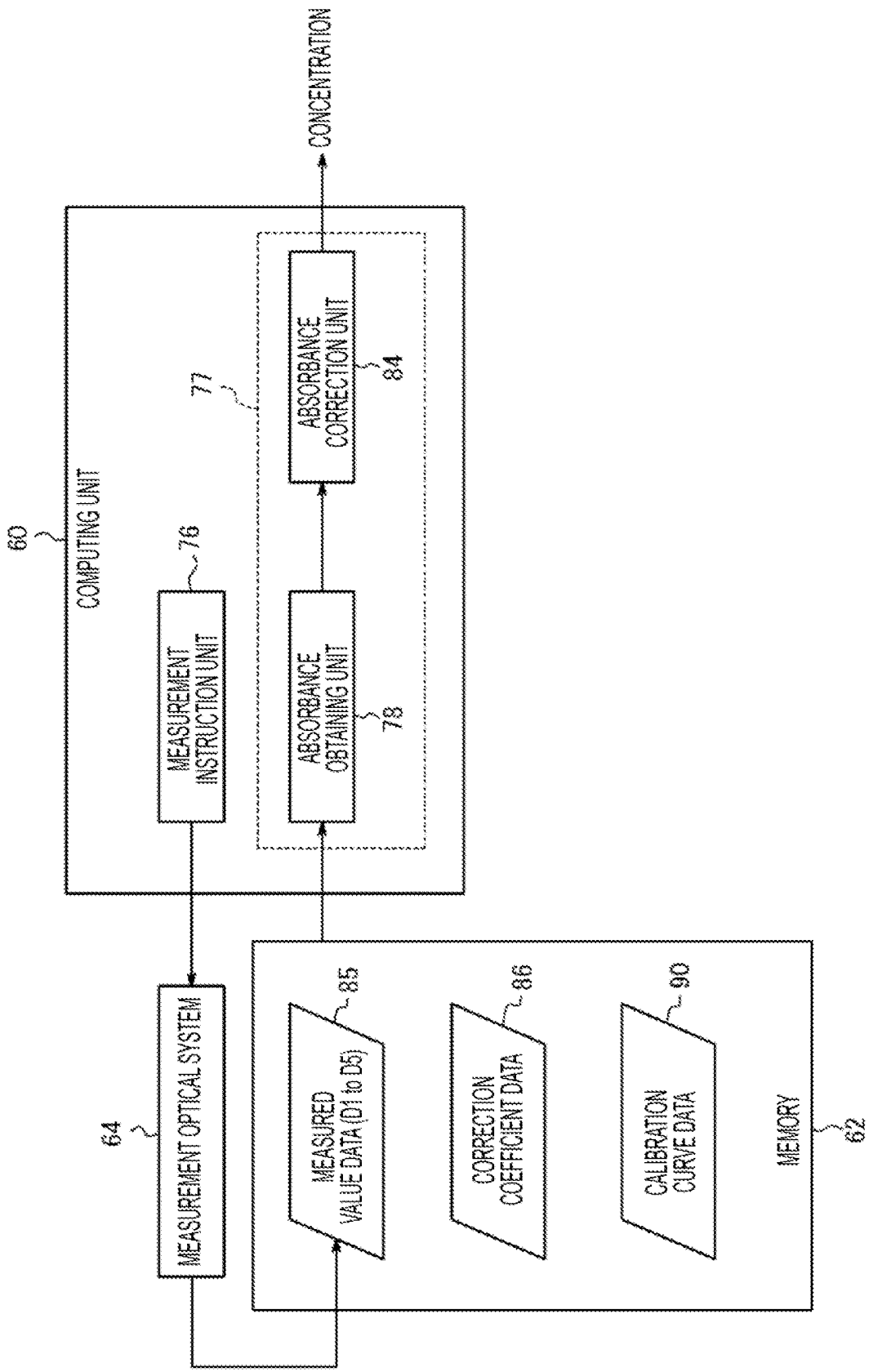
FIG. 6 is a functional block diagram of a computing unit illustrated in FIG. 5.

FIG. 6 is a functional block diagram of the computing unit 60 illustrated in FIG. 5. The computing unit 60 allows a measurement instruction unit 76 and a concentration measurement unit 77 to function. The measurement instruction unit 76 is configured to instruct measuring operations of the measurement optical system 64, and the concentration measurement unit 77 is configured to measure a concentration of the component of interest with various data.

The concentration measurement unit 77 includes an absorbance obtaining unit 78 and an absorbance correction unit 84.

In FIG. 6, the memory 62 stores measured value data 85 of a first measured value D1 to a fifth measured value D5, correction coefficient data 86, and calibration curve data 90. The measured value data 85 indicates absorbance of the mixture X at each of the first wavelength $\lambda 1$ to the fifth wavelength $\lambda 5$ measured by the measurement optical system 64. The correction coefficient data 86 includes a group of correction coefficients correlated with the absorbance of the mixture X at each of the first wavelength $\lambda 1$ to the fourth wavelength $\lambda 4$. The calibration curve data 90 includes a calibration curve representing a relationship between various physical quantities (for example, a glucose concentration) and absorbance of the pigmentary component in the mixture X obtained by correcting, based on the correction coefficient data 86, the absorbance of the mixture X actually measured at the fifth wavelength $\lambda 5$, and a calibration curve representing a relationship between absorbance of hemoglobin in the mixture X and a hematocrit level. The term "hematocrit level" is a percentage of a volume ratio of a hemocyte component in blood to the blood (whole blood).

Hereinafter described is the component measurement method according to an embodiment of the present invention, in which a color reaction between glucose, a component of interest in blood, and the coloring reagent 22 is carried out with the blood (whole blood) and the coloring reagent 22 without separating a plasma component including the glucose from the blood, and in which absorbance at a predetermined measuring wavelength of a pigmentary component colored by the color reaction between the glucose and the coloring reagent 22 is estimated based on absorbance at various wavelengths of the whole mixture X obtained by the color reaction.

First, problems in estimating a component of interest in blood based on absorbance measurement using the blood (whole blood) will be described with reference to FIGS. 7 and 8. In the following Examples, a mixed reagent of glucose dehydrogenase (GDH), a tetrazolium salt (WST-4), and an electron mediator was used as the coloring reagent 22.

Figure 7:
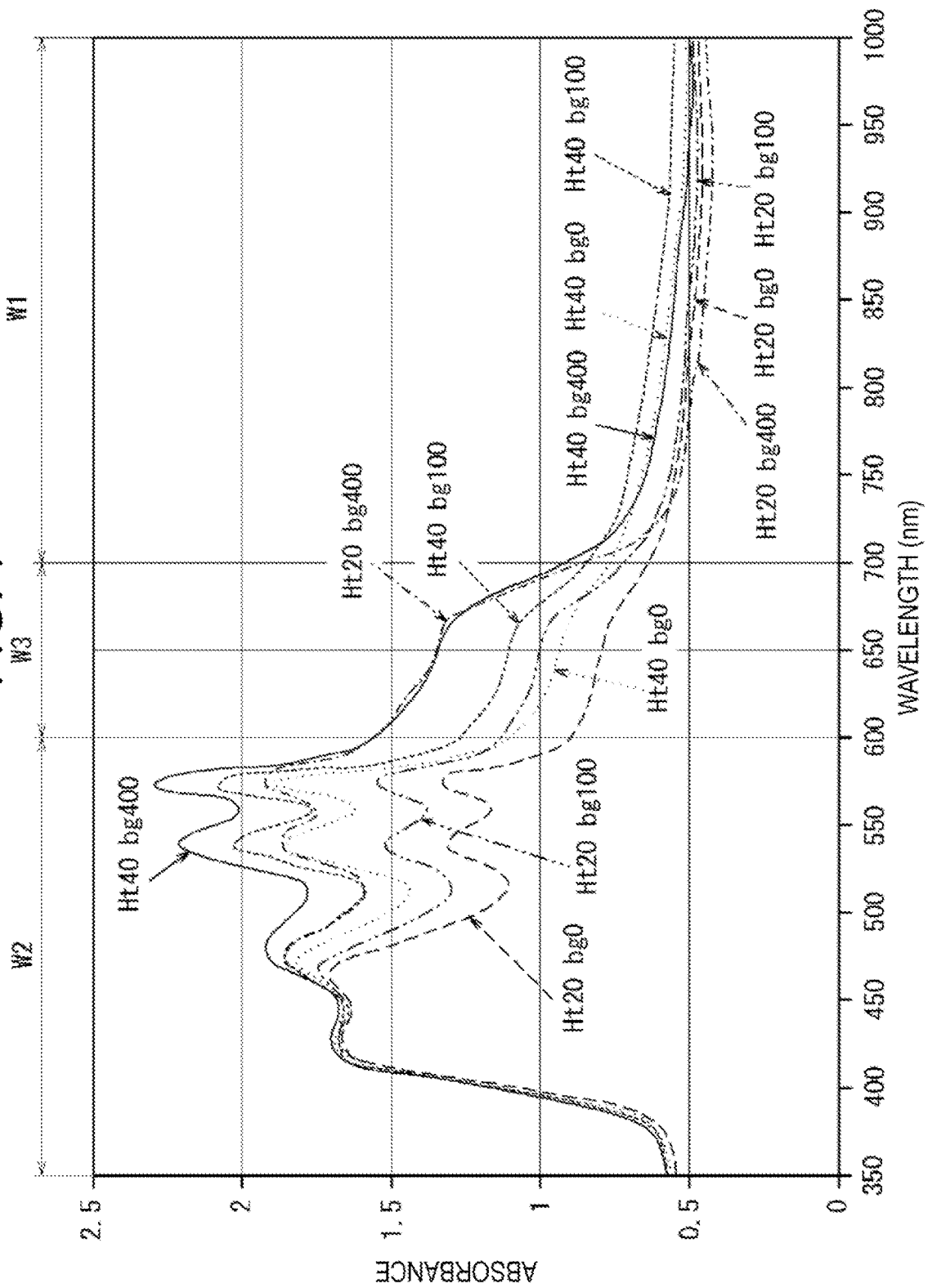
FIG. 7 is a view illustrating absorbance spectra of six kinds of mixtures obtained by a color reaction between each of six kinds of blood samples and a reagent.

FIG. 7 illustrates absorbance spectra of six kinds of mixtures X each of which is obtained by a color reaction between each of six kinds of blood samples and the coloring reagent 22. A hematocrit level and a glucose concentration of each blood sample are known. These six kinds of blood samples are referred to as first to sixth samples. The first sample has a hematocrit level of 20% and a glucose concentration of 0 mg/dL (denoted as "Ht20 bg0" in FIG. 7). The second sample has a hematocrit level of 20% and a glucose concentration of 100 mg/dL (denoted as "Ht20 bg100" in FIG. 7). The third sample has a hematocrit level of 20% and a glucose concentration of 400 mg/dL (denoted as "Ht20 bg400" in FIG. 7). The fourth sample has a hematocrit level of 40% and a glucose concentration of 0 mg/dL (denoted as "Ht40 bg0" in FIG. 7). The fifth sample has a hematocrit level of 40% and a glucose concentration of 100 mg/dL (denoted as "Ht40 bg100" in FIG. 7). The sixth sample has a hematocrit level of 40% and a glucose concentration of 400 mg/dL (denoted as "Ht40 bg400" in FIG. 7).

Figure 8:
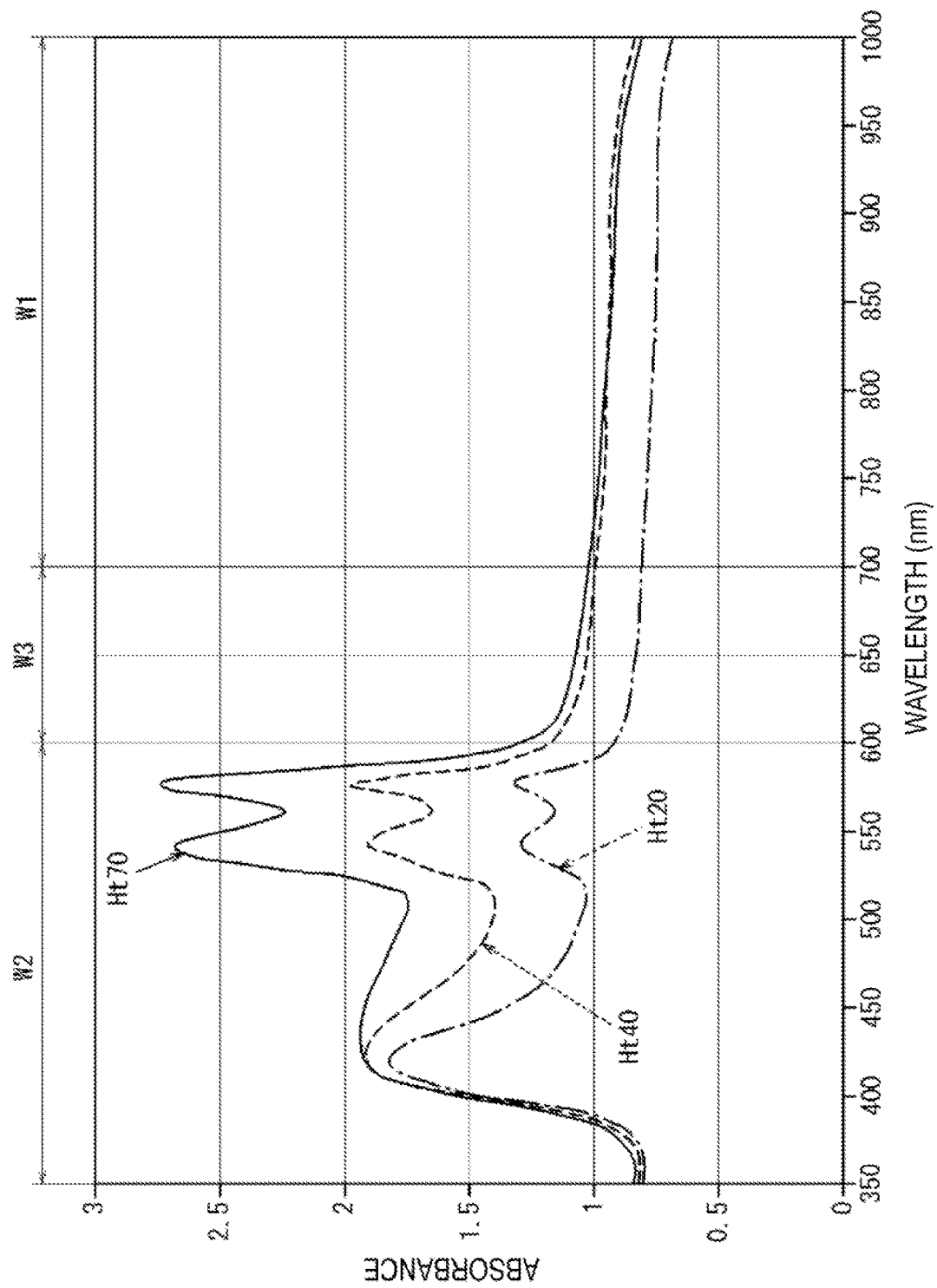
FIG. 8 is a view illustrating absorbance spectra of seven kinds of blood samples.

FIG. 8 illustrates absorbance spectra of seven kinds of blood samples whose hematocrit level and glucose concentration are known. These seven kinds of blood samples are referred to as first to seventh samples. The first to sixth samples are the same as the first to sixth samples illustrated in FIG. 7. The seventh sample has a hematocrit level of 70% and a glucose concentration of 100 mg/dL. Blood samples with an equal hematocrit level have a substantially equivalent absorbance spectrum so that FIG. 8 illustrates only three curves that have different hematocrit levels. Specifically, three curves illustrated in FIG. 8 represent the samples having the hematocrit level of 20% (denoted as "Ht20" in FIG. 8), 40% (denoted as "Ht40" in FIG. 8), and 70% (denoted as "Ht70" in FIG. 8).

When a sample includes components other than the pigmentary component of interest for absorbance measurement, optical phenomena generally occur, which may affect measurement results of the pigmentary component. For example, due to occurrence of "light scattering" due to a hemocyte component in blood, particulates such as dust adhered to a surface of a component measurement chip or the component measurement chip, or the like and due to occurrence of "light absorption" due to a pigmentary component other than the pigmentary component of interest (specifically, hemoglobin), it is likely that absorbance larger than a true value is measured.

Specifically, the absorbance spectra of the blood samples illustrated in FIG. 8 mainly have two peaks around 540 nm and around 570 nm. These two peaks are chiefly caused by light absorption of oxygenated hemoglobin in erythrocytes. In the absorbance spectra of the blood samples illustrated in FIG. 8, each absorbance gradually decreases in a substantially straight line as the wavelength becomes longer at a wavelength band of 600 nm or more. The substantially straight line is chiefly caused by light scattering of the hemocyte component, the particulates such as dust adhered to the component measurement chip, and the like.

In other words, effects of the light scattering due to the hemocyte component and the like is dominant in the absorbance of each blood sample at a wavelength band longer than the wavelength around 600 nm. In regard to the absorbance of each blood sample at a wavelength band shorter than the wavelength around 600 nm, effects of the light absorption due to the hemoglobin is dominant rather than the effects of the light scattering due to the hemocyte component and the like.

On the other hand, similarly to the absorbance spectra of the blood samples illustrated in FIG. 8, the absorbance spectra of the mixtures X illustrated in FIG. 7 each have the trend curve with the absorbance gradually decreasing as the wavelength becomes longer. However, as compared with the curves illustrated in FIG. 8, the absorbance spectra of the mixtures X illustrated in FIG. 7 show high absorbance around a wavelength band of visible light, about 600 nm to 700 nm. This high absorbance in the range of 600 nm to 700 nm chiefly results from light absorption characteristics of the pigmentary component colored by the color reaction between the blood glucose and the coloring reagent 22.

In this manner, when accurately measuring the absorbance derived from the pigmentary component, using not only the pigmentary component of interest but also the mixture X containing blood having the light absorption characteristics illustrated in FIG. 8, it is required to eliminate effects (noise) such as the light scattering due to the hemocyte component and the like, and the light absorption due to the hemoglobin from a measured value of absorbance at a predetermined measuring wavelength (for example, 650 nm).

More specifically, it is necessary to estimate the effects (noise) such as the light scattering due to the hemocyte component and the like, and the light absorption due to the hemoglobin at a predetermined measuring wavelength (for example, 650 nm) at which absorptivity of the pigmentary component of interest is high, whereby correcting a measured value of absorbance at the measuring wavelength.

Hereinafter, the component measurement method carried out by the component measurement device 1 will be described in detail.

The component measurement device 1 is configured to measure the component of interest in the blood based on the optical properties of the mixture X containing the pigmentary component colored by the color reaction between the blood and the coloring reagent 22 as a reagent. Specifically, in this embodiment, a glucose concentration in the plasma component in the blood is measured.

Furthermore, the component measurement device 1 is configured to correct the measured value of the absorbance of the mixture X at the measuring wavelength, based on the optical properties due to the hemocyte component in the blood and the particulates such as dust adhered to the surface of the component measurement chip 2 or the component measurement chip 2 and based on a ratio between the reduced hemoglobin and the oxygenated hemoglobin in erythrocytes, so as to calculate a glucose concentration in the blood. In other words, the component measurement method carried out by the component measurement device 1 involves a step of correcting the measured value of the absorbance of the mixture X at the measuring wavelength based on information of the scattered light due to the hemocyte component in the blood and the particulates such as dust adhered to the surface of the component measurement chip 2 or the component measurement chip 2 and based on the ratio between the reduced hemoglobin and the oxygenated hemoglobin in erythrocytes.

Figure 9:
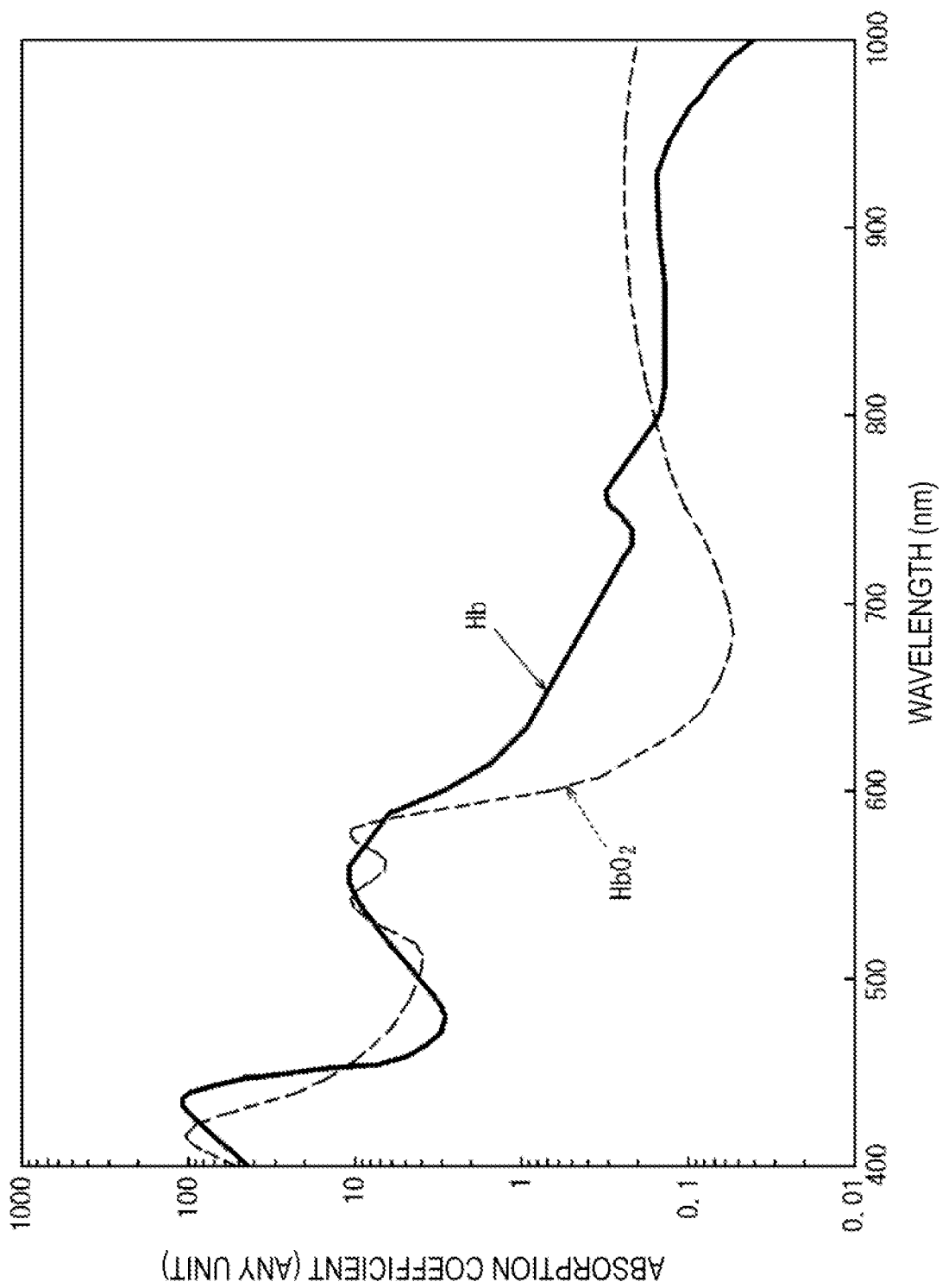
FIG. 9 is a view illustrating an absorption coefficient of reduced hemoglobin and an absorption coefficient of oxygenated hemoglobin.

FIG. 9 illustrates an absorption coefficient of the reduced hemoglobin (denoted as "Hb" in FIG. 9) and an absorption coefficient of the oxygenated hemoglobin (denoted as "HbO$_2$" in FIG. 9). Hemoglobin in erythrocytes mainly includes oxygenated hemoglobin combined with oxygen, and reduced hemoglobin in which oxygen is dissociated in a place with small oxygen partial pressure. As reduced hemoglobin passes through lungs and combines with oxygen, oxygenated hemoglobin plays a role of transporting oxygen into body through arteries and is mainly observable in arterial blood. For example, when collecting blood from a finger pad, the collected blood is from capillary so that the blood contains a relatively large amount of oxygenated hemoglobin. Conversely, reduced hemoglobin is mainly observable in venous blood.

Figure 10:
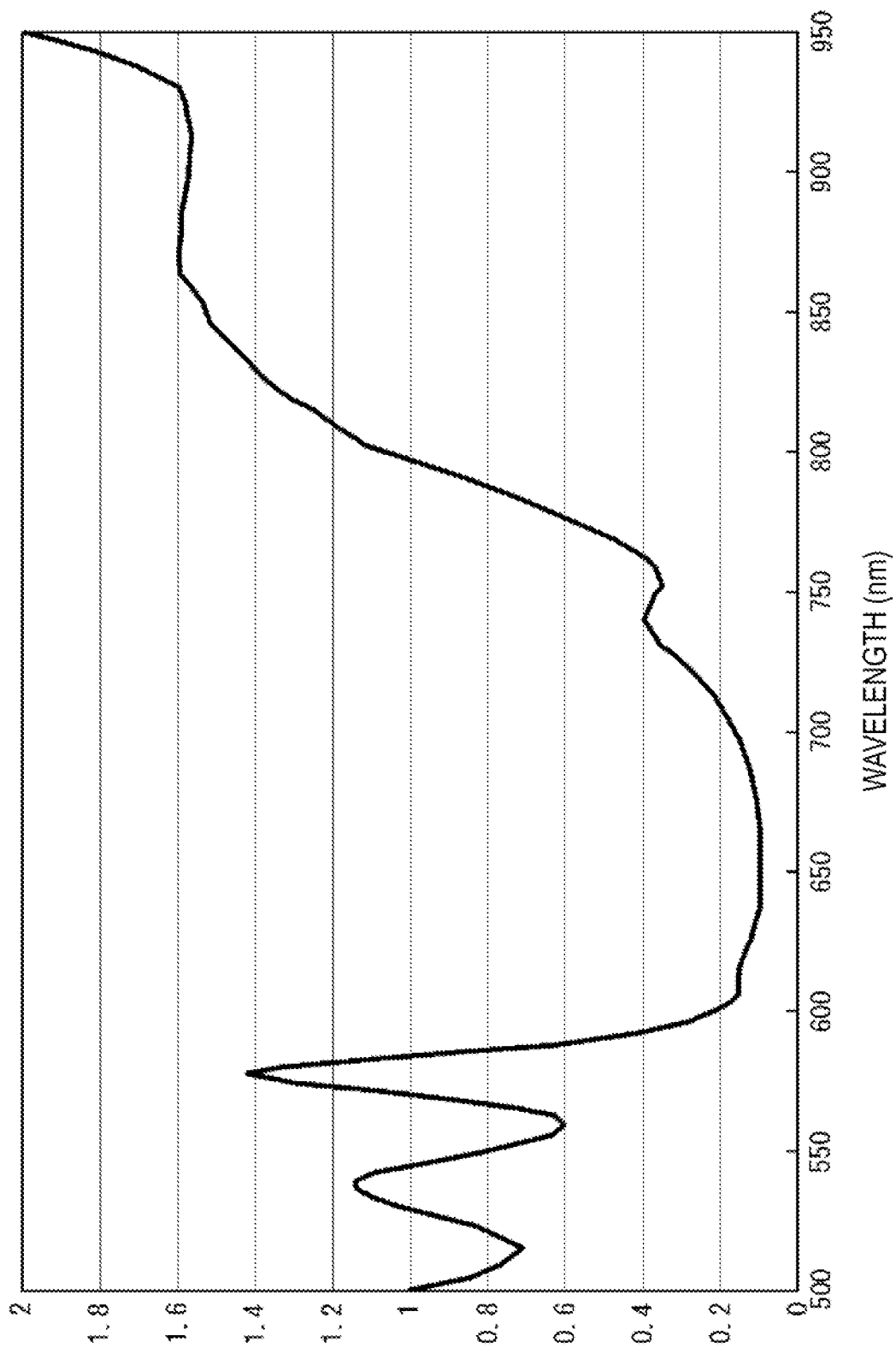
FIG. 10 is a view illustrating a ratio of the absorption coefficient of the oxygenated hemoglobin to the absorption coefficient of the reduced hemoglobin.

In an existing technique, it is typical to correct the absorbance obtained at the measuring wavelength corresponding to the pigmentary component of interest, using, for example, a hematocrit level, without considering the ratio between the reduced hemoglobin and the oxygenated hemoglobin. However, as illustrated in FIG. 9, the absorption coefficient of the reduced hemoglobin does not coincide with the absorption coefficient of the oxygenated hemoglobin, and an absorbed amount of the reduced hemoglobin and an absorbed amount of the oxygenated hemoglobin differ depending on wavelengths. FIG. 10 is a view illustrating a ratio of the absorption coefficient of the oxygenated hemoglobin to the absorption coefficient of the reduced hemoglobin. For example, when the measuring wavelength for measuring the absorbance of the pigmentary component of interest is 650 nm, the absorption coefficient of the reduced hemoglobin is about 0.9, and the absorption coefficient of the oxygenated hemoglobin is about 0.09. In other words, the absorption coefficient of the oxygenated hemoglobin corresponds to about 10% of the absorption coefficient of the total hemoglobin. In order to estimate the absorbance derived from the pigmentary component of interest more accurately, it is important to consider the ratio between the reduced hemoglobin and the oxygenated hemoglobin.

Therefore, in the component measurement device 1, the measuring wavelength for measuring the absorbance of the pigmentary component contained in the mixture X is set to 650 nm, and from the measured value of the absorbance of the mixture X measured at this measuring wavelength, the effects caused by the light scattering of the hemocyte component and the like and the effects caused by the light absorption of the hemoglobin, in which the ratio between the reduced hemoglobin and the oxygenated hemoglobin is taken into account, are eliminated. Accordingly, the absorbance of the pigmentary component contained in the mixture X is estimated, and the calibration curve representing the relationship between this estimated absorbance and a glucose concentration is used so as to derive the glucose concentration.

Hereinafter, the component measurement method carried out by the component measurement device 1 will be described in more detail.

The coloring reagent 22 used in this embodiment is one having a peak around 600 nm in the absorbance of the pigmentary component colored by the color reaction with the blood glucose. In this embodiment, the measuring wavelength for measuring the absorbance of the pigmentary component is set to 650 nm.

The measuring wavelength for measuring the absorbance of the pigmentary component of interest may be a wavelength at which absorptivity of the pigmentary component is relatively high and the effects caused by the light absorption of the hemoglobin are relatively small. Specifically, the measuring wavelength may be within a wavelength band W3 that corresponds to the full width at half maximum of a peak wavelength band in the absorbance spectrum of the pigmentary component of interest and in which a ratio of absorbance depending on the light absorption of the hemoglobin to the total absorbance is relatively small (see FIGS. 7 and 8). When the full width at half maximum of the peak wavelength band in the absorbance spectrum is specified, the phrase a wavelength band that "corresponds to the full width at half maximum in a peak wavelength band" represents a range from a wavelength indicating a half width on the short-wavelength side to a wavelength indicating a half width on the long-wavelength side. In the absorbance spectrum of the pigmentary component of interest in this embodiment, the peak wavelength is around 600 nm, and a wavelength band from about 500 nm to about 700 nm corresponds to the full width at half maximum. Furthermore, the effects caused by the light absorption of the hemoglobin in the total absorbance are relatively small at the wavelength band of 600 nm or more. Therefore, in this embodiment, in regard to the wavelength band W3 that corresponds to the full width at half maximum of the peak wavelength band in the absorbance spectrum of the pigmentary component of interest and in which the ratio of absorbance depending on the light absorption of the hemoglobin to the total absorbance is relatively small, it is set to 600 nm or more and 700 nm or less. The measuring wavelength is not limited to 650 nm in this embodiment. Another wavelength ranging from 600 nm to 700 nm may be used as the measuring wavelength. At a wavelength band where a signal indicating the absorbance of the pigmentary component is strong and at which the ratio of absorbance depending on the light absorption of the hemoglobin to the total absorbance is very small, the absorbance derived from the pigmentary component is measured more accurately so that it is preferable to set the measuring wavelength to a wavelength around 650 nm, which is slightly longer than the wavelength around 600 nm, the peak wavelength of the absorbance spectrum of the pigmentary component. More specifically, the measuring wavelength preferably ranges from 630 nm to 680 nm, more preferably from 640 nm to 670 nm. Particularly, the measuring wavelength is preferably 650 nm as in this embodiment. A preferable example of such a pigmentary component includes a tetrazolium salt, and, for example, WST-4 is most preferable.

Furthermore, this embodiment employs the coloring reagent 22 in which the full width at half maximum of the peak wavelength band in the absorbance spectrum of the pigmentary component is about 500 nm to about 700 nm. However, in other embodiments, a coloring reagent having the full width at half maximum of a peak wavelength band within a range different from the above range may be employed. However, as described above, in consideration of the light absorption characteristics of the hemoglobin, it is desirable that the measuring wavelength in the absorbance spectrum of the pigmentary component does not overlap with the wavelength band where the absorbance depending on the light absorption of the hemoglobin becomes large (600 nm or less).

Hereinafter, a method for estimating the absorbance of the pigmentary component at 650 nm, the measuring wavelength of this embodiment, will be described. The component measurement device 1 measures the absorbance of the mixture X at the first wavelength $\lambda 1$ to the fourth wavelength $\lambda 4$, the four wavelengths different from the measuring wavelength (650 nm). Using the four measured values, the first measured value D1 to fourth measured value D4 and the predetermined correction coefficient data 86, the component measurement device 1 corrects the fifth measured value D5 of the absorbance of the mixture X at the measuring wavelength so as to estimate the absorbance of the pigmentary component at the measuring wavelength. Hereinafter, for convenience sake, the measuring wavelength is described as a "fifth wavelength $\lambda 5$".

Specifically, as the four measured values, the first measured value D1 to the fourth measured value D4, the component measurement device 1 uses the first measured value D1 and the second measured value D2, which are two measured values of the absorbance of the mixture X at the first wavelength $\lambda 1$ and the second wavelength $\lambda 2$, which are two wavelengths longer than the fifth wavelength $\lambda 5$ or the measuring wavelength; and the third measured value D3 and the fourth measured value D4, which are two measured values of the absorbance of the mixture X at the third wavelength $\lambda 3$ and the fourth wavelength $\lambda 4$, which are two wavelengths shorter than the fifth wavelength $\lambda 5$ or the measuring wavelength.

More specifically, as the four measured values, the first measured value D1 to the fourth measured value D4, the component measurement device 1 uses the first measured value D1 and the second measured value D2, which are two measured values of the absorbance of the mixture X at the first wavelength $\lambda 1$ and the second wavelength $\lambda 2$, which are two wavelengths within a wavelength band longer than the fifth wavelength $\lambda 5$ or the measuring wavelength, at which the effects caused by the light scattering of the hemocyte component and the like are dominant in the total absorbance; and the third measured value D3 and the fourth measured value D4, which are two measured values of the absorbance of the mixture X at the third wavelength $\lambda 3$ and the fourth wavelength $\lambda 4$, which are two wavelengths within a wavelength band shorter than the fifth wavelength $\lambda 5$ or the measuring wavelength, at which the effects caused by the light absorption of the hemoglobin are large in the total absorbance.

In other words, as the first measured value D1 and the second measured value D2, the component measurement device 1 uses the first measured value D1 and the second measured value D2, which are two measured values of the absorbance of the mixture X at the first wavelength $\lambda 1$ and the second wavelength $\lambda 2$, which are within a wavelength band longer than the measuring wavelength that is within a wavelength band corresponding to the full width at half maximum of the peak wavelength band in the absorbance spectrum of the pigmentary component of interest (500 nm to 700 nm in this embodiment), that is, for example, a long wavelength band W1 longer than the wavelength band W3.

In addition, as the third measured value D3 and the fourth measured value D4, the component measurement device 1 uses the third measured value D3 and the fourth measured value D4, the absorbance of the mixture X at the third wavelength $\lambda 3$ and the fourth wavelength $\lambda 4$, which are within a wavelength band shorter than the measuring wavelength that is within a wavelength band corresponding to the full width at half maximum of the peak wavelength band in the absorbance spectrum of the pigmentary component of interest (500 nm to 700 nm), that is, for example, a short wavelength band W2 shorter than the wavelength band W3.

The absorbance obtaining unit 78 of the component measurement device 1 obtains the first measured value D1 to the fifth measured value D5. Specifically, the mixture X is irradiated by the first to fifth light sources 67a to 67d and 68 of the light emitting unit 66 with emitted light including emission wavelengths of the first wavelength $\lambda 1$ to the fifth wavelength $\lambda 5$. The light receiving unit 72 receives transmitted light of each emitted light that passes through the mixture X. The computing unit 60 calculates the absorbance of the mixture X at each wavelength from the relationship between the emitted light and the transmitted light and stores in the memory 62 the first measured value D1 to the fifth measured value D5, the absorbance of the mixture X at each wavelength, as the measured value data 85. The absorbance obtaining unit 78 of the component measurement device 1 can obtain the measured value data 85 from the memory 62. A way for the absorbance obtaining unit 78 to obtain the first measured value D1 to the fifth measured value D5 is not limited to the above way. Those values may be obtained by various known means.

The absorbance correction unit 84 of the component measurement device 1 corrects the fifth measured value D5, using the first measured value D1 to the fourth measured value D4, and estimates the absorbance of the pigmentary component at the fifth wavelength $\lambda 5$ or the measuring wavelength (650 nm in this example).

Particularly, as seen from FIGS. 7 and 8, the absorbance spectrum of the mixture X is substantially linear at the long wavelength band W1 at which the effects caused by the light scattering of the hemocyte component and the like are dominant so that when the first measured value D1, the absorbance at the first wavelength $\lambda 1$, and the second measured value D2, the absorbance at the second wavelength $\lambda 2$, are obtained, it is possible to estimate noise excluding the absorbance of the pigmentary component at the fifth wavelength $\lambda 5$ or the measuring wavelength, to some extent by determining a slope between the first measured value D1 and the second measured value D2. The component measurement device 1 is configured to derive a glucose concentration in blood in consideration of the ratio between the reduced hemoglobin and the oxygenated hemoglobin in erythrocytes as well as the optical properties due to the hemocyte component and the like in the blood. Therefore, the component measurement device 1 is capable of performing correction with higher accuracy, using two wavelengths (the third wavelength and the fourth wavelength) selected in accordance with to the ratio between the reduced hemoglobin and the oxygenated hemoglobin.

Specifically, a wavelength at which a difference in absorption coefficient between the reduced hemoglobin and the oxygenated hemoglobin is equal to or less than a first predetermined value is used as the third wavelength $\lambda 3$, and a wavelength at which the difference in absorption coefficient between the reduced hemoglobin and the oxygenated hemoglobin is larger than the first predetermined value is used as the fourth wavelength $\lambda 4$. More specifically, a wavelength at which a ratio of the absorption coefficient of the oxygenated hemoglobin to the absorption coefficient of the reduced hemoglobin (see FIG. 10) is equal to or more than a first threshold, a predetermined threshold, is used as the third wavelength $\lambda 3$, and a wavelength at which the ratio of the absorption coefficient of the oxygenated hemoglobin to the absorption coefficient of the reduced hemoglobin is less than the first threshold is used as the fourth wavelength $\lambda 4$. In other words, as the third wavelength $\lambda 3$ and the fourth wavelength $\lambda 4$, the following two wavelengths are used: the wavelength at which the ratio of the absorption coefficient of the oxygenated hemoglobin to the absorption coefficient of the reduced hemoglobin is equal to or more than the first threshold; and the wavelength at which the ratio is less than the first threshold. Accordingly, when correcting the fifth measured value D5 with the first measured value D1 to the fourth measured value D4, the absorbance correction unit 84 is capable of performing highly accurate correction in consideration of the ratio between the reduced hemoglobin and the oxygenated hemoglobin.

As the two wavelengths selected in accordance with the ratio between the reduced hemoglobin and the oxygenated hemoglobin, it is preferable to use two wavelengths at which a difference in light absorption of the hemoglobin depending on the ratio between the reduced hemoglobin and the oxygenated hemoglobin is large. Therefore, as the third wavelength $\lambda 3$, this embodiment employs a wavelength at which the ratio of the absorption coefficient of the oxygenated hemoglobin to the absorption coefficient of the reduced hemoglobin is 0.8 or more, that is, a wavelength in a range of 520 nm to 550 nm, or in a range of 565 nm to 585 nm. As the fourth wavelength $\lambda 4$, it is preferable to use a wavelength at which the ratio of the absorption coefficient of the oxygenated hemoglobin to the absorption coefficient of the reduced hemoglobin is less than 0.8, that is, a wavelength more than 550 nm and less than 565 nm, or more than 585 nm and less than 600 nm. However, as the third wavelength $\lambda 3$, it is preferable to use a wavelength at which the absorption coefficient of the reduced hemoglobin and the absorption coefficient of the oxygenated hemoglobin are equal so that it is possible to simultaneously estimate the amount of the whole hemoglobin and the hematocrit level. In other words, in this embodiment, it is preferable to use, as the third wavelength $\lambda 3$, a wavelength around 530 nm, around 545 nm, around 570 nm, or around 580 nm, and it is particularly preferable to use a wavelength ranging from 540 to 545 nm where the absorption coefficient of the whole hemoglobin is large. Furthermore, as the fourth wavelength $\lambda 4$, it is preferable to use a wavelength more than 550 nm and less than 565 nm, particularly, around 560 nm where the difference in absorption coefficient is a maximum. Alternatively, it is preferable to use a wavelength more than 585 nm and less than 600 nm, particularly, around 590 nm where the difference in absorption coefficient is a maximum.

In this manner, using the third wavelength $\lambda 3$ and the fourth wavelength $\lambda 4$ at which the difference in the light absorption of the whole hemoglobin is large at the short wavelength band W2 where the light absorption of the whole hemoglobin largely varies depending on the ratio between the reduced hemoglobin and the oxygenated hemoglobin, it is possible to accurately estimate noise excluding the absorbance of the pigmentary component at the fifth wavelength $\lambda 5$ or the measuring wavelength (650 nm in this embodiment), in consideration of the ratio between the reduced hemoglobin and the oxygenated hemoglobin. Therefore, according to the component measurement device 1, the absorbance of the pigmentary component at the fifth wavelength $\lambda 5$ or the measuring wavelength, and the component of interest (glucose concentration in this embodiment) are measured with accuracy.

It should be noted that, in this embodiment, only the third wavelength $\lambda 3$ and the fourth wavelength $\lambda 4$ are set to wavelengths in which the effects of the ratio between the reduced hemoglobin and the oxygenated hemoglobin are taken into account. In addition to the third wavelength $\lambda 3$ and the fourth wavelength $\lambda 4$, it is more preferable to use similar wavelengths as the first wavelength $\lambda 1$ and the second wavelength $\lambda 2$.

Specifically, as the first wavelength $\lambda 1$ within the long wavelength band W1 where the light scattering of the hemocyte component and the like is dominant, a wavelength at which the difference in absorption coefficient between the reduced hemoglobin and the oxygenated hemoglobin is equal to or less than a second predetermined value is used, and as the second wavelength $\lambda 2$ similarly within the long wavelength band W1, a wavelength band where the difference is larger than the second predetermined value is used. More specifically, as the first wavelength $\lambda 1$ within the long wavelength band W1, it is preferable to use a wavelength at which the ratio of the absorption coefficient of the oxygenated hemoglobin to the absorption coefficient of the reduced hemoglobin is equal to or more than the first threshold and equal to or lower than the second threshold, and as the second wavelength $\lambda 2$ similarly within the long wavelength band W1, it is preferable to use a wavelength at which the ratio of the absorption coefficient of the oxygenated hemoglobin to the absorption coefficient of the reduced hemoglobin is less than the first threshold or more than the second threshold. It should be noted that the second threshold is another predetermined threshold larger than the first threshold. In other words, as the first wavelength $\lambda 1$ and the second wavelength $\lambda 2$, it is preferable to use two wavelengths where the ratio of the absorption coefficient of the oxygenated hemoglobin to the absorption coefficient of the reduced hemoglobin is different. Accordingly, when correcting the fifth measured value D5 with the first measured value D1 to the fourth measured value D4, the absorbance correction unit 84 is capable of performing highly accurate correction in which the ratio between the reduced hemoglobin and the oxygenated hemoglobin is further taken into account.

Particularly, at the long wavelength band W1, the effects caused by the light scattering of the hemocyte component and the like are dominant, but the light absorption of the hemoglobin also affects in the extent similar to the measuring wavelength of the component of interest. Therefore, as the first wavelength $\lambda 1$ and the second wavelength $\lambda 2$, it is preferable to use two wavelengths at which the light absorption of the hemoglobin varies relatively largely in accordance with the ratio between the reduced hemoglobin and the oxygenated hemoglobin.

Therefore, in this embodiment, it is preferable to use, as the first wavelength $\lambda 1$, a wavelength within a range where the ratio of the absorption coefficient of the oxygenated hemoglobin to the absorption coefficient of the reduced hemoglobin is 0.8 or more and 1.5 or less, preferably within a range from 790 nm to 850 nm. However, it is particularly preferable that the first wavelength $\lambda 1$ is selected from around the wavelength where the light absorption of the hemoglobin is relatively large at the long wavelength band W1 and where the absorption coefficient of the reduced hemoglobin is equal to the absorption coefficient of oxygenated hemoglobin. In this embodiment, it is particularly preferable to use a wavelength from 800 nm to 810 nm.

In this embodiment, it is preferable to use, as the second wavelength $\lambda 2$, a wavelength at which the ratio of the absorption coefficient of the oxygenated hemoglobin to the absorption coefficient of the reduced hemoglobin is less than 0.8 or more than 1.5. A refractive index (scatter characteristics) of a medium (herein, hemocytes) and the light absorption of the hemoglobin also vary depending on wavelengths so that using a wavelength close to the measuring wavelength as the second wavelength $\lambda 2$ enables estimation of the effects caused by the light scattering of the hemocyte component and the like and the light absorption of the hemoglobin at the measuring wavelength (650 nm in this embodiment) with more accuracy. In other words, in this embodiment, it is preferable to use a wavelength shorter than the first wavelength $\lambda 1$. More specifically, in this embodiment, it is preferable to use a wavelength more than 700 nm and less than 790 nm as the second wavelength $\lambda 2$.

Furthermore, the second wavelength $\lambda 2$ is set to a wavelength within the long wavelength band W1 where the absorbance of the pigmentary component included in the total absorbance at the second wavelength $\lambda 2$ is 10% or less, preferably 6% or less, more preferably 3% or less, still more preferably substantially 0%, of the absorbance of the pigmentary component included in the total absorbance at the measuring wavelength. In other words, it is particularly preferable to use a wavelength equal to or longer than a wavelength that is the bottom of the long-wavelength side of the peak wavelength band in the absorbance spectrum of the pigmentary component. This eliminates the effects of the light absorption of the pigmentary component and enables accurate estimation of the noise in which the effects caused by the light scattering of the hemocyte component and the like are dominant at the long wavelength band W1. Therefore, in this embodiment, it is more preferable to use a wavelength of 725 nm or more and less than 790 nm as the second wavelength $\lambda 2$. Since the wavelength closer to the measuring wavelength is most preferable as the second wavelength $\lambda 2$, it is particularly preferable to use, as the second wavelength $\lambda 2$, a wavelength at which the absorbance of the pigmentary component is zero, that is, the bottom of the long-wavelength side of the peak wavelength band in the absorbance spectrum of the pigmentary component. Therefore, in this embodiment, it is particularly preferable to use 755 nm as the second wavelength $\lambda 2$. The term "total absorbance" of "the absorbance of the pigmentary component included in the total absorbance" indicates the absorbance of the whole mixture. The expression "the absorbance of the pigmentary component" of "the absorbance of the pigmentary component included in the total absorbance" indicates the absorbance of a reactant generated by the color reaction between the component of interest in the blood and the pigmentary component in the reagent, that is, the absorbance derived from the pigmentary component in the mixture.

As described above, using the first measured value D1 to fourth measured value D4, the measured values of the absorbance of the mixture X at the first wavelength $\lambda 1$ to the fourth wavelength $\lambda 4$, the component measurement device 1 corrects the fifth measured value D5, the measured value of the absorbance of the mixture X at the measuring wavelength, so as to estimate the absorbance of the pigmentary component at the measuring wavelength.

Hereinafter, a correction method carried out by the absorbance correction unit 84 of the component measurement device 1 will be described.

As described above, the memory 62 of the component measurement device 1 stores the measured value data 85 of the first measured value D1 to the fifth measured value D5, which indicates the absorbance of the mixture X at each of the first wavelength $\lambda 1$ to the fifth wavelength $\lambda 5$ measured by the measurement optical system 64; the correction coefficient data 86, which includes a group of correction coefficients correlated with the absorbance of the mixture X at each of the first wavelength $\lambda 1$ to the fourth wavelength $\lambda 4$; and the calibration curve data 90, which includes a calibration curve representing a relationship between various physical quantities and the absorbance of the pigmentary component in the mixture X obtained by correcting the absorbance of the mixture X actually measured at the fifth wavelength $\lambda 5$ based on the correction coefficient data 86.

The absorbance correction unit 84 derives the absorbance of the pigmentary component at the fifth wavelength $\lambda 5$ or the measuring wavelength, based on the measured value data 85 and the correction coefficient data 86 stored in the memory 62.

The correction coefficient data 86 herein is derived by regression analysis computed in advance based on the following Formula 1.

$$B(\lambda 5)=b0+b1*B(\lambda 1)+b2*B(\lambda 2)+b3*B(\lambda 3)+b4*B(\lambda 4) \quad \text{[Formula 1]}$$

The symbol $B(\lambda)$ represents noise excluding the absorbance of the pigmentary component at a wavelength $\lambda$, and the coefficients b0, b1, b2, b3, and b4 are derived by regression calculation based on the Formula 1, using various kinds of blood samples. Specifically, in this embodiment, based on the selection criteria of the first wavelength $\lambda 1$ to the fourth wavelength $\lambda 4$, wavelengths of 810 nm, 750 nm, 545 nm, 560 nm are used as the first wavelength $\lambda 1$, the second wavelength $\lambda 2$, the third wavelength $\lambda 3$, and the fourth wavelength $\lambda 4$, respectively. Various kinds of blood samples are prepared based on six blood samples having different component compositions. Each sample has a hematocrit level adjusted from 10% to 70%. The absorbance spectrum of each adjusted blood sample is measured so as to derive the coefficients b0, b1, b2, b3, and b4 by regression analysis. The total number of observations herein is 766 times. Based on these derived coefficients b0 to b4, the group of correction coefficients correlated with the absorbance of the mixture X at each of the first wavelength λ1 to the fourth wavelength λ4 is derived. Using the correction coefficient data 86 including the correction coefficients, the measured value of the absorbance of the mixture X at 650 nm, the measuring wavelength, is corrected from the measured values of the absorbance of the mixture X at 545 nm, 560 nm, 750 nm, and 810 nm so that the absorbance of the pigmentary component at 650 nm can be estimated.

Herein, each of the coefficients b0 to b4 obtained by the regression calculation can be determined as a value specific to a measurement system, not varying depending on hematocrit levels. Therefore, the numerical values (measured values) of B(λ1) to B(λ4) used in the regression calculation fluctuate depending on hematocrit levels.

Figure 11:
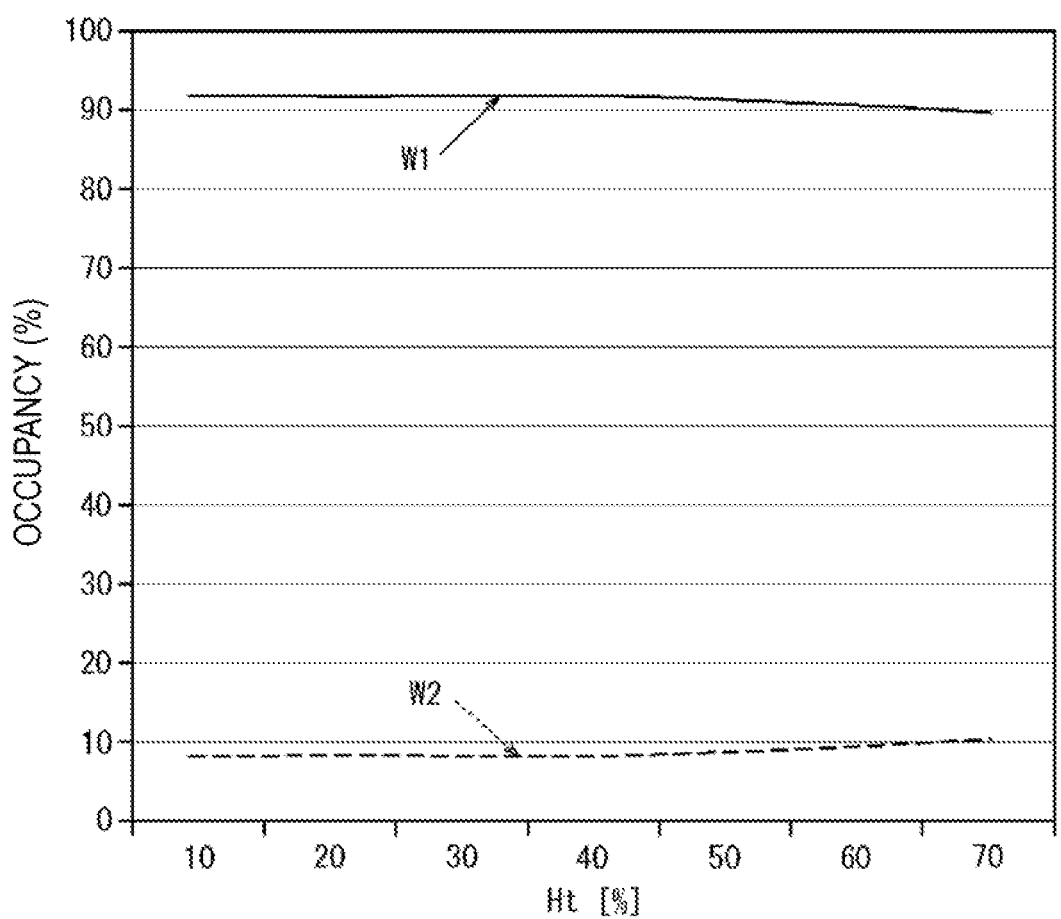
FIG. 11 is a graph illustrating occupancy at a long wavelength band and occupancy at a short wavelength band regarding absorbance of components other than a pigmentary component at a measuring wavelength estimated by regression analysis.

FIG. 11 is a graph illustrating the degree of effect depending on measured values at the long wavelength band W1 (denoted as "W1" in FIG. 11) and the degree of effect depending on measured values at the short wavelength band W2 (denoted as "W2" in FIG. 11) in the absorbance (noise) of components other than the pigmentary component at the measuring wavelength in the regression calculation. It should be noted that the "degree of effect" herein represents the occupancy of data. As illustrated in FIG. 11, considering the results of the measured data obtained by the regression calculation, when the absorbance (noise) of components other than the pigmentary component at the measuring wavelength is estimated with the first measured value D1 to the fourth measured value D4, the degree of effect in each of the first measured value D1 and the second measured value D2 at the first wavelength λ1 and the second wavelength λ2 within the long wavelength band W1 decreases from 92% to 90% as the hematocrit level increases from 10% to 70% (see "W1" in FIG. 11). On the other hand, the degree of effect in each of the third measured value D3 and the fourth measured value D4 at the third wavelength λ3 and the fourth wavelength λ4 within the short wavelength band W2 increases from 8% to 10% as the hematocrit level increases from 10% to 70% (see "W2" in FIG. 11). In this manner, the changes in the degree of effect at the long wavelength band W1 and at the short wavelength band W2 depending on hematocrit levels enables accurate estimation of the absorbance (noise) of components other than the pigmentary component at the measuring wavelength. Accordingly, it is possible to estimate the absorbance of the pigmentary component at the measuring wavelength more accurately. When the absorption of the pigmentary component is included in the first measured value D1 to the fourth measured value D4, it is required to correct the first measured value D1 to the fourth measured value D4 and calculate B(λ), the absorbance (noise) of components other than the pigment component.

In the component measurement device 1, when using, as the third wavelength λ3, a wavelength at which the absorption coefficient of the reduced hemoglobin is equal to the absorption coefficient of the oxygenated hemoglobin at the short wavelength band W2 where the effects caused by the light absorption of the hemoglobin is overwhelmingly large (in FIG. 9, 530 nm, 545 nm, 570 nm, or 580 nm), the hematocrit level can be derived from the third measured value D3 or from the third measured value D3 and the first measured value D1 obtained by the wavelength at which the absorption coefficient of the reduced hemoglobin is equal to the absorption coefficient of the oxygenated hemoglobin (in FIG. 9, 800 nm) at the long wavelength band W1 where the effects caused by the light scattering of the hemocyte component and the like are large. The hematocrit level can be derived from the calibration curve of the absorbance of the hemoglobin and the hematocrit level stored in the memory 62.

Hereinafter described is results of verification experiments regarding accuracy of the absorbance of the pigmentary component at the measuring wavelength that is estimated in the component measurement device 1 based on the optical properties including the scattered light caused by dust or the hemocyte component and the like in the blood and based on the ratio between the reduced hemoglobin and the oxygenated hemoglobin in erythrocytes. The samples (n=7) were prepared by adjusting the hematocrit level of each blood to 10%, 20%, 30%, 40%, 50%, 60%, and 70%.

Figure 12A:
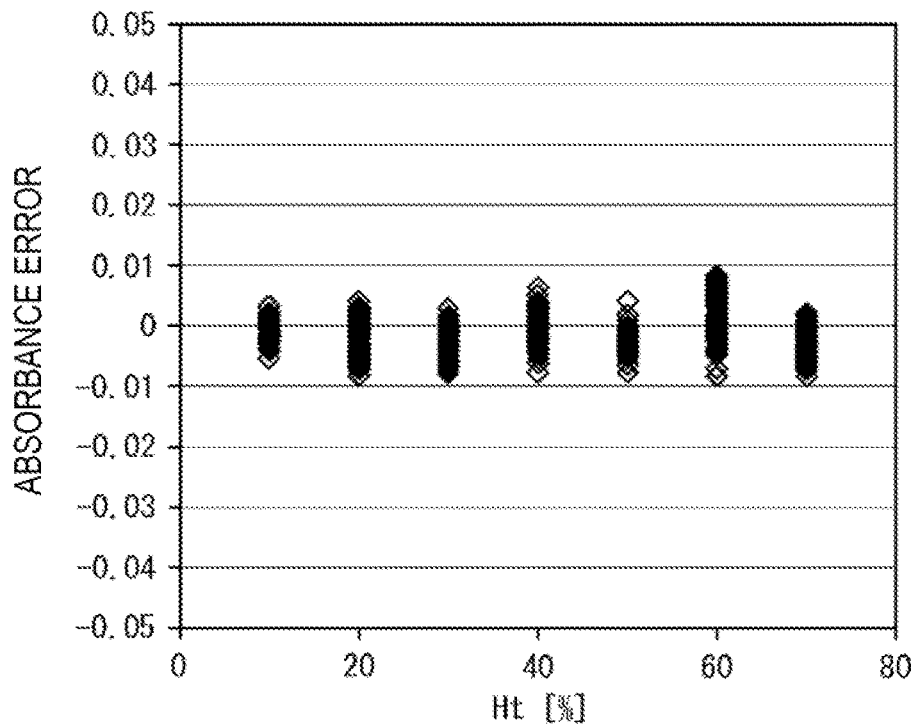
FIG. 12($a$) is a graph illustrating errors between absorbance measured by a component measurement method according to an embodiment of the present invention and a true value, and FIG. 12($b$) is a graph illustrating errors between absorbance measured by a component measurement method according to Comparative Example and a true value.
Figure 12B:
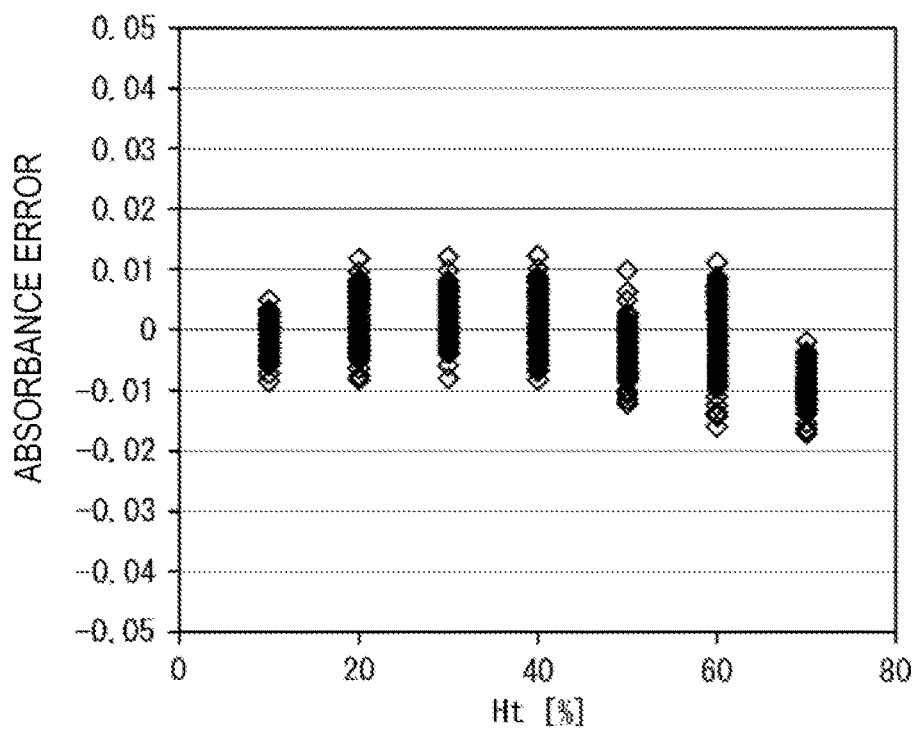

FIG. 12(*a*) is a graph illustrating errors between the absorbance of components other than the pigmentary component at the measuring wavelength derived by the component measurement method of the component measurement device 1 when wavelengths of 810 nm, 750 nm, 545 nm, 560 nm, and 650 nm are used as the first wavelength λ1, the second wavelength λ2, the third wavelength λ3, the fourth wavelength λ4, and the fifth wavelength λ5 or the measuring wavelength, respectively, and a true value of the absorbance of components other than the pigmentary component at the measuring wavelength. It should be noted that, in this Example, the absorbance of the pigmentary component included in the total absorbance at the second wavelength λ2 corresponds to 3% of the absorbance at the measuring wavelength. On the contrary, as Comparative Example, FIG. 12(*b*) is a graph illustrating errors between the absorbance of components other than the pigmentary component at the measuring wavelength (650 nm) derived by a similar method using two wavelengths from the first wavelength λ1 to the fourth wavelength λ4, 810 nm and 750 nm, and a true value of the absorbance of components other than the pigmentary component at the measuring wavelength.

In the errors illustrated in FIG. 12(*a*), 0.0058 is double the standard error, whereas 0.0109 is double the standard error in the errors illustrated in FIG. 12(*b*), indicating that the errors illustrated in FIG. 12(*a*) are smaller than the errors illustrated in FIG. 12(*b*). In other words, according to the component measurement method carried out by the component measurement device 1 of this embodiment, it is possible to estimate the absorbance of the pigmentary component at the measuring wavelength with higher accuracy than the case where the absorbance is estimated from only the two wavelengths (810 nm and 750 nm in the verification experiments) within the long wavelength band W1. It should be noted that, in this Example, when the hematocrit level is 40%, an absorbance error 0.001 corresponds to an error of 1 mg/dL in blood glucose level. Using the component measurement method, the component measurement device 1 is capable of reducing measurement errors in blood glucose level with respect to blood having a wide hematocrit level from 10% to 70%.

Figure 13:
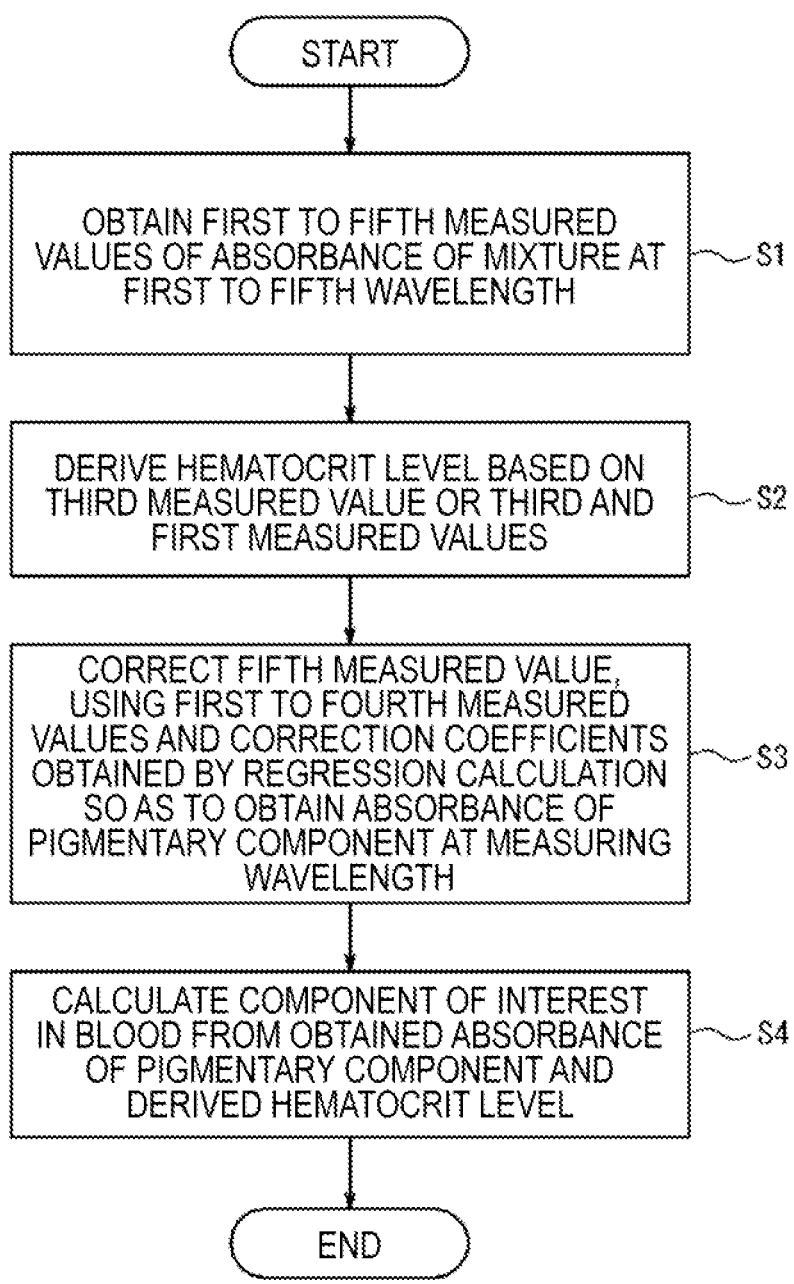
FIG. 13 is a flowchart illustrating the component measurement method according to an embodiment of the present invention.

Finally, the component measurement method of the component measurement device 1 will be described with reference to FIG. 13. FIG. 13 is a flowchart illustrating the component measurement method carried out by the component measurement device 1.

This component measurement method involves Step S1 to obtain the first measured value D1, the absorbance of the mixture X at the first wavelength λ1, the second measured value D2, the absorbance of the mixture X at the second wavelength λ2, the third measured value D3, the absorbance of the mixture X at the third wavelength λ3, the fourth measured value D4, the absorbance of the mixture X at the fourth wavelength λ4, and the fifth measured value D5, the absorbance of the mixture X at the fifth wavelength λ5; Step S2 to derive a hematocrit level based on at least one of the first measured value D1 to the fifth measured value D5; Step S3 to correct the fifth measured value D5 based on the first measured value D1 to the fourth measured value D4 and correction coefficients obtained by regression calculation so as to obtain the absorbance of the pigmentary component at the measuring wavelength; and Step S4 to calculate the component of interest in the blood from the absorbance of the pigmentary component at the measuring wavelength and the hematocrit level derived.

In Step S1, as described above, the first measured value D1 to the fifth measured value D5 are obtained with the light emitting unit 66 and the light receiving unit 72 of the measurement optical system 64. In this embodiment, in Step S2, a hematocrit level is derived based on the third measured value D3 or based on the third measured value D3 and the first measured value D1. Specifically, in Step S2, the absorbance of hemoglobin is estimated from the third measured value D3 or from the third measured value D3 and the first measured value D1 so as to derive a hematocrit level. Furthermore, when the third measured value D3 or the third measured value D3 and the first measured value D1 include absorption of the pigmentary component, the hematocrit level is derived from a corrected value obtained by correction calculation in which an amount of absorption of the pigmentary component is subtracted from the third measured value D3 or from the third measured value D3 and the first measured value D1, respectively. In this embodiment, the hematocrit level is derived from the calibration curve representing the relationship between the absorbance of hemoglobin and the hematocrit level in the mixture X stored in the memory 62. In Step S3, the fifth measured value D5 is actually corrected based on the first measured value D1 to the fourth measured value D4 and the correction coefficients obtained by the regression calculation so as to estimate and obtain the absorbance of the pigmentary component at the measuring wavelength. Finally, in Step S4, a glucose concentration is calculated from the obtained absorbance of the pigmentary component at the measuring wavelength and the hematocrit level derived by the calibration curve representing the relationship with the glucose concentration.

Hereinafter described is a case in which another coloring reagent different from the coloring reagent 22 is used. The coloring reagent 22 described above is a mixed reagent of glucose dehydrogenase (GDH), a tetrazolium salt (WST-4), and an electron mediator, but the coloring reagent described below is a tetrazolium salt A represented by the following Chemical Formula 1. In the Formula, X=Na.

[Chemical Formula 1]

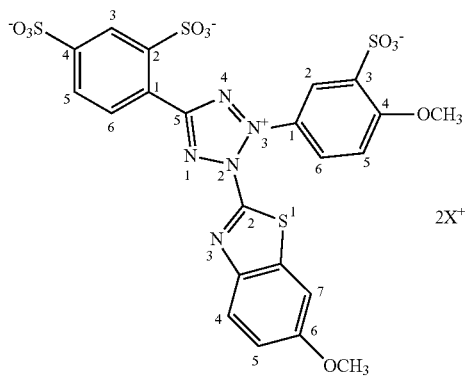

Figure 14:
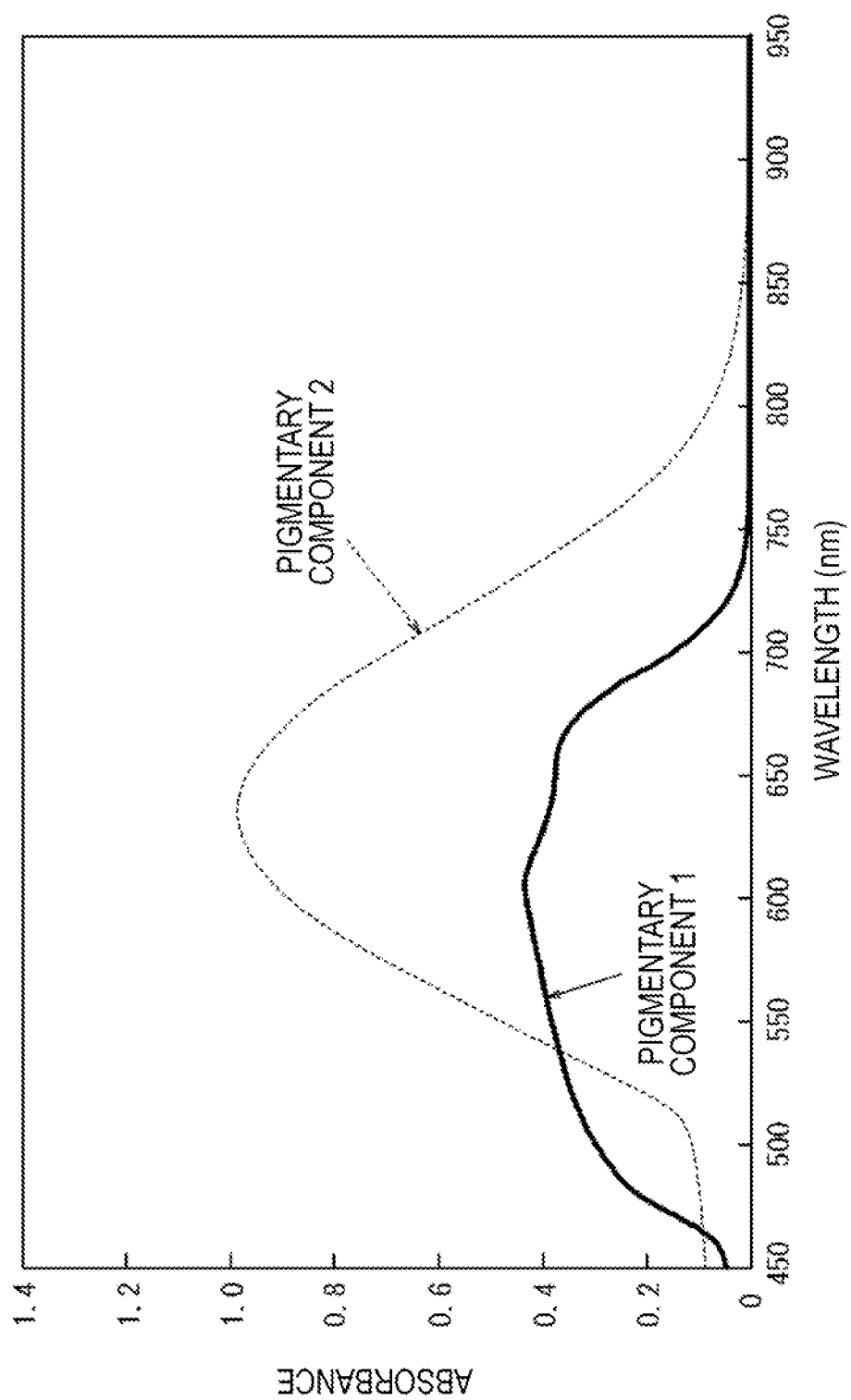
FIG. 14 is a view illustrating absorbance spectra of two pigmentary components.

FIG. 14 is a view illustrating absorbance spectrum of WST-4, which is the pigmentary component contained in the coloring reagent 22 (denoted as "pigmentary component 1" in FIG. 14) and absorbance spectrum of the tetrazolium salt A, which is the pigmentary component contained in the coloring reagent described below (denoted as "pigmentary component 2" in FIG. 14) when glucose water having a glucose concentration of 300 mg/dL is used as a sample.

As illustrated in FIG. 14, the absorbance spectrum of the tetrazolium salt A has an absorption peak larger and much clearer than the absorbance spectrum of WST-4. Accordingly, utilizing the absorption peak of the coloring reagent containing the tetrazolium salt A, a signal representing the absorbance of the pigmentary component is detected more easily than in a case of utilizing an absorption peak of the coloring reagent 22 containing WST-4 so that it is possible to reduce measurement errors of the component of interest. The peak wavelength of the tetrazolium salt A is about 650 nm so that, as similar to the above example, 650 nm may be used as the fifth wavelength λ5 or the measuring wavelength. However, as illustrated in FIG. 14, the peak wavelength band of the tetrazolium salt A shifts closer to the long-wavelength side than the peak wavelength band of WST-4. Therefore, when using the same wavelength as the second wavelength λ2 in the above example, measurement errors of the component of interest tend to occur because of considerable effects caused by light absorption of the tetrazolium salt A.

When using the coloring reagent containing the tetrazolium salt A as the pigmentary component, used as the second wavelength λ2 is a wavelength within a wavelength band where effect caused by the light absorption of the coloring reagent is small. Specifically, when using the coloring reagent containing the tetrazolium salt A, the second wavelength λ2 is set to a wavelength within the long wavelength band W1 where the absorbance of the pigmentary component included in the total absorbance at the second wavelength λ2 is 10% or less, preferably 6% or less, more preferably 3% or less, still more preferably substantially 0%, of the absorbance of the pigmentary component included in the total absorbance at the measuring wavelength. Therefore, in this example, when the measuring wavelength is set to 650 nm, it is preferable to use a wavelength of 790 nm or more, more preferably 810 nm or more, still more preferably 830 nm or more, and particularly preferably 920 nm or more.

From a viewpoint of characteristics of a versatile light source such as the LED element that is actually used herein, the second wavelength λ2 is preferably 950 nm or less, and more preferably 940 nm or less.

It should be noted that, in regard to the first wavelength λ1, the third wavelength λ3, the fourth wavelength λ4, and the fifth wavelength λ5, wavelength bands similar to those illustrated in the above example may be employed. When a component measurement method similar to the aforementioned method is carried out with the first wavelength λ1 to the fifth wavelength λ5, correction is performed in accordance with the optical properties due to the hemocyte component and the like in the blood and in accordance with the ratio between the reduced hemoglobin and the oxygenated hemoglobin in erythrocytes, which leads to highly accurate measurement results.

Herein, from the assumption that the coloring reagent containing the tetrazolium salt A was used, regression analysis was performed by the Formula 1 in the above example, using wavelengths of 810 nm, 900 nm, 545 nm, and 560 nm as the first wavelength λ1, the second wavelength λ2, the third wavelength λ3, and the fourth wavelength λ4, respectively, based on the selection criteria of the first wavelength $\lambda 1$ to the fourth wavelength $\lambda 4$. A method for regression analysis is similar to one described in the above example.

Figure 15:
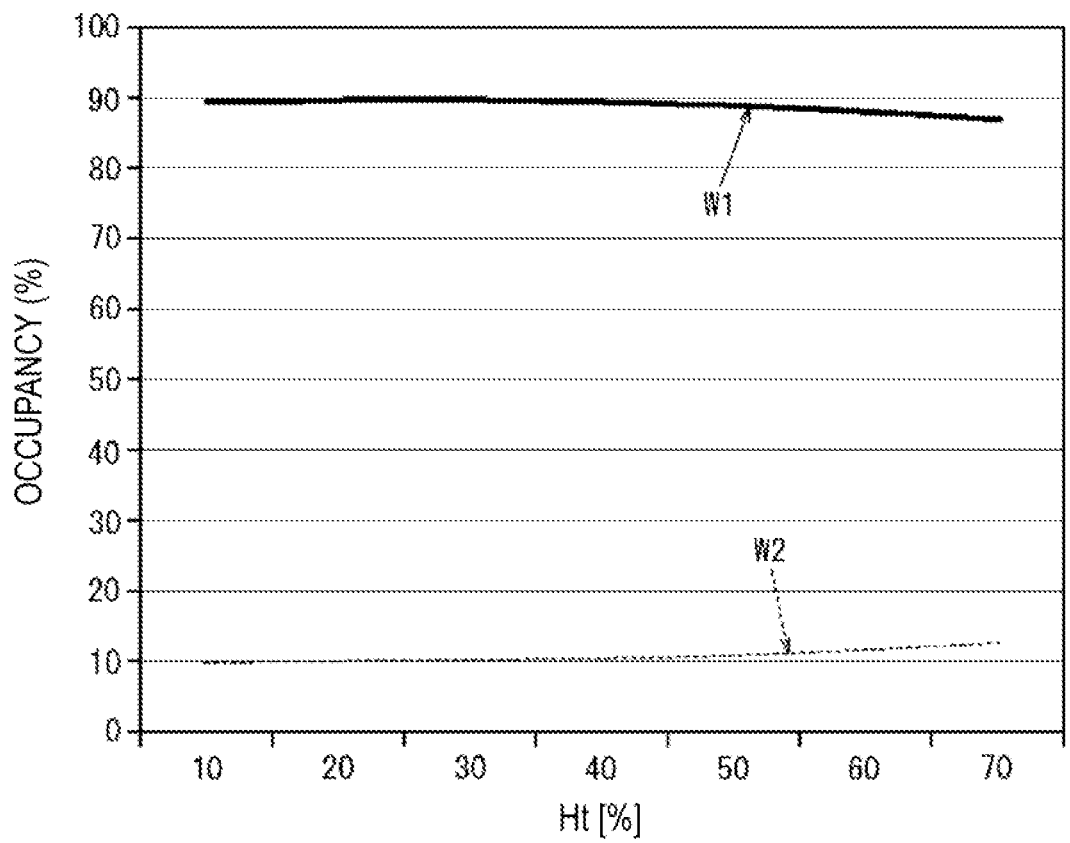
FIG. 15 is a graph illustrating occupancy at a long wavelength band and occupancy at a short wavelength band regarding absorbance of components other than a pigmentary component at a measuring wavelength estimated by regression analysis.

FIG. 15 is a graph illustrating the degree of effect depending on measured values at the long wavelength band W1 (denoted as "W1" in FIG. 15) and the degree of effect depending on measured values at the short wavelength band W2 (denoted as "W2" in FIG. 15) in the absorbance (noise) of components other than the pigmentary component at the measuring wavelength in the regression calculation. It should be noted that the "degree of effect" herein represents the occupancy of data as described above. As illustrated in FIG. 15, considering the results of measured data obtained by the regression calculation, it is found that similar results are obtained as in the above example. Specifically, when the absorbance (noise) of components other than the pigmentary component at the measuring wavelength is estimated with the first measured value D1 to the fourth measured value D4, the degree of effect in each of the first measured value D1 and the second measured value D2 at the first wavelength $\lambda 1$ and the second wavelength $\lambda 2$ within the long wavelength band W1 decreases from 90% to 88% as the hematocrit level increases from 10% to 70% (see "W1" in FIG. 15). On the other hand, the degree of effect in each of the third measured value D3 and the fourth measured value D4 at the third wavelength $\lambda 3$ and the fourth wavelength $\lambda 4$ within the short wavelength band W2 increases from 10% to 12% as the hematocrit level increases from 10% to 70% (see "W2" in FIG. 15). In this manner, the changes in the degree of effect at the long wavelength band W1 and at the short wavelength band W2 depending on hematocrit levels enables accurate estimation of the absorbance (noise) of components other than the pigmentary component at the measuring wavelength. Accordingly, it is possible to estimate the absorbance of the pigmentary component at the measuring wavelength more accurately. It should be noted that, when the absorption of the pigmentary component is included in the first measured value D1 to the fourth measured value D4, it is required to correct the first measured value D1 to the fourth measured value D4 and to calculate $B(\lambda)$, the absorbance (noise) of components other than the pigmentary component.

Hereinafter described is results of verification experiments regarding accuracy of the absorbance of the pigmentary component at the measuring wavelength that is estimated based on the optical properties due to the hemocyte component and the like in the blood and based on the ratio between the reduced hemoglobin and the oxygenated hemoglobin in erythrocytes, using the coloring reagent containing the tetrazolium salt A. The samples (n=7) were prepared by adjusting the hematocrit level of each blood to 10%, 20%, 30%, 40%, 50%, 60%, and 70%.

Figure 16A:
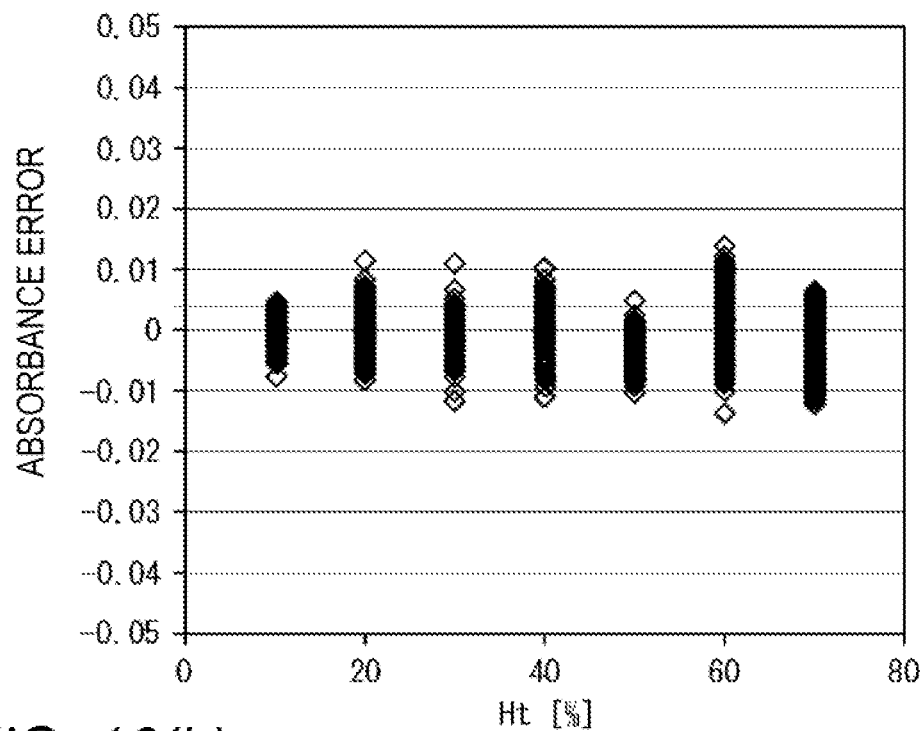
FIG. 16($a$) is a graph illustrating errors between absorbance measured by the component measurement method according to an embodiment of the present invention and a true value, and FIG. 16($b$) is a graph illustrating errors between absorbance measured by the component measurement method according to Comparative Example and a true value.

FIG. 16(a) is a graph illustrating errors between the absorbance of components other than the pigmentary component at the measuring wavelength derived by the component measurement method of the component measurement device 1 when wavelengths of 810 nm, 900 nm, 545 nm, 560 nm, and 650 nm are used as the first wavelength $\lambda 1$, the second wavelength $\lambda 2$, the third wavelength $\lambda 3$, the fourth wavelength $\lambda 4$, and the fifth wavelength $\lambda 5$ or the measuring wavelength, respectively, and a true value of the absorbance of components other than the pigmentary component at the measuring wavelength. In this example, the absorbance of the pigmentary component included in the total absorbance at the second wavelength $\lambda 2$ corresponds to 1% of the absorbance included in the total absorbance at the measuring wavelength. On the contrary, as Comparative Example, FIG. 16(b) is a graph illustrating errors between the absorbance of components other than the pigmentary component at a measuring wavelength (650 nm) derived by a similar method using only two wavelengths, 810 nm and 900 nm, from the first wavelength $\lambda 1$ to fourth wavelength $\lambda 4$ and a true value of the absorbance of components other than the pigmentary component at the measuring wavelength.

Figure 16B:
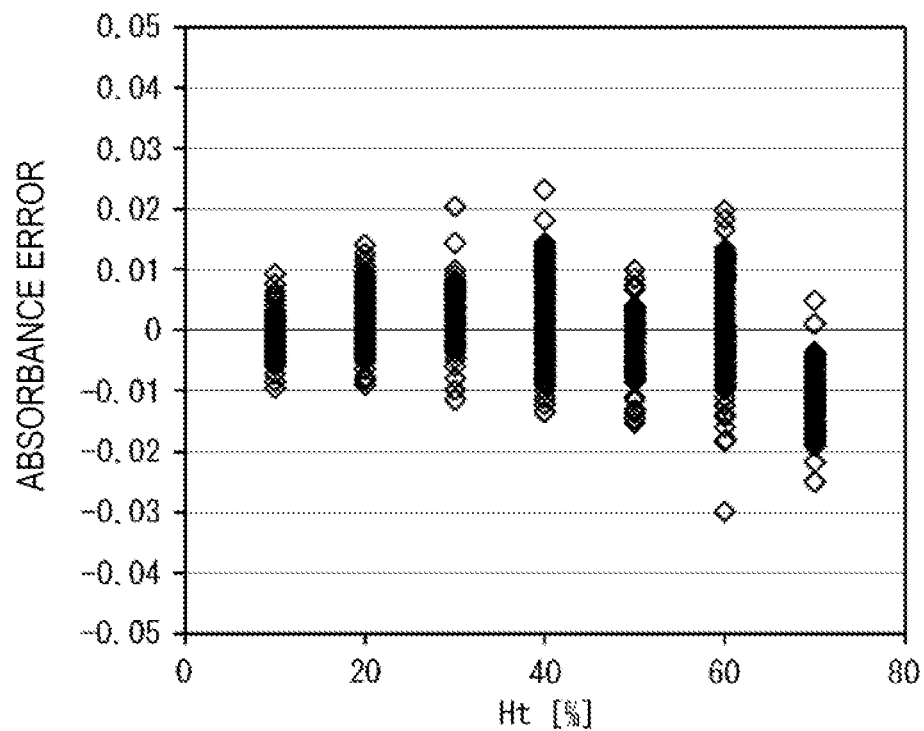

In the errors illustrated in FIG. 16(a), 0.0085 is double the standard error, whereas 0.0140 is double the standard error in the errors illustrated in FIG. 16(b), indicating that the errors illustrated in FIG. 16(a) are smaller than the errors illustrated in FIG. 16(b). In other words, regardless of types of the coloring reagent, according to the component measurement method carried out by the component measurement device 1, it is possible to estimate the absorbance with higher accuracy than the absorbance of the pigmentary component at the measuring wavelength estimated from only two wavelengths (810 nm and 900 nm in the verification experiments) within the long wavelength band W1. It should be noted that, in this example, when the hematocrit level is set to 40%, an absorbance error 0.002 corresponds to an error of 1 mg/dL in blood glucose level. Using the component measurement method, the component measurement device 1 is capable of reducing measurement errors in blood glucose level with respect to blood having a wide hematocrit level from 10% to 70%.

It should be noted that, as described above, the second wavelength $\lambda 2$ in this example is 900 nm, within a wavelength band longer than 750 nm, which is the second wavelength $\lambda 2$ in the above example. Therefore, the second wavelength $\lambda 2$ in the case of using the coloring reagent containing the tetrazolium salt A is apart from 650 nm, the measuring wavelength, compared to the second wavelength $\lambda 2$ in the case of using the coloring reagent 22 containing WST-4. From this point of view, the condition is likely to cause the measurement errors. However, as illustrated in FIG. 14, the absorption peak of the tetrazolium salt A is larger than that of WST-4 so that the signal representing the absorbance of the pigmentary component is detected more easily. Depending on the intensity of the signal, it is possible to prevent an increase in measurement errors caused by the second wavelength $\lambda 2$ being apart from the measuring wavelength. Accordingly, even with the second wavelength $\lambda 2$ being apart from the measuring wavelength, the measurement errors of the component of interest can be reduced.

The component measurement device, the component measurement method, and the component measurement program according to the present invention are not limited to the specific descriptions in the aforementioned embodiment and may be modified into various embodiments within the gist of the scope of claims.

In the embodiment, a glucose concentration is measured to measure glucose or a component of interest. However, the present invention is not limited to the measurement of a concentration, and other physical quantities may be measured. In the embodiment, glucose in a plasma component is exemplified as a component of interest in blood, but the present invention is not limited thereto. For example, cholesterol in the blood may be the component of interest. Therefore, the component measurement device is not limited to the blood glucose level measurement device.

Furthermore, in the embodiment, different types of first to fifth light sources 67a to 67d and 68 are used as the light emitting unit 66. However, a single light source and different of types of optical filters (of bandpass type) provided in front of the light source may be used in combination. Alternatively, a single light source and different of types of light receiving units may be combined. Still further, in the embodiment, the light receiving unit 72 is configured to receive transmitted light that passes through the component measurement chip 2. However, the light receiving unit 72 may be configured to receive reflected light reflected from the component measurement chip 2.

The present disclosure relates to a component measurement device, a component measurement method, and a component measurement program. Particularly, the present disclosure relates to a component measurement device, a component measurement method, and a component measurement program for measuring a component of interest in blood.

REFERENCE NUMERAL LIST

1 COMPONENT MEASUREMENT DEVICE
2 COMPONENT MEASUREMENT CHIP
10 HOUSING
10a MAIN BODY
10b CHIP ATTACHING PORTION
11 DISPLAY UNIT
12 DETACHMENT LEVER
13 POWER BUTTON
14 OPERATION BUTTON
21 BASE MEMBER
22 COLORING REAGENT (REAGENT)
23 FLOW PATH
24 SUPPLY UNIT
25 COVER MEMBER
26 EJECTOR PIN
60 COMPUTING UNIT
62 MEMORY
63 POWER SUPPLY CIRCUIT
64 MEASUREMENT OPTICAL SYSTEM
66 LIGHT EMITTING UNIT
67a TO 67d FIRST LIGHT SOURCE TO FOURTH LIGHT SOURCE
68 FIFTH LIGHT SOURCE
70 LIGHT EMISSION CONTROL CIRCUIT
72 LIGHT RECEIVING UNIT
74 LIGHT RECEPTION CONTROL CIRCUIT
76 MEASUREMENT INSTRUCTION UNIT
77 CONCENTRATION MEASUREMENT UNIT
78 ABSORBANCE OBTAINING UNIT
84 ABSORBANCE CORRECTION UNIT
85 MEASURED VALUE DATA
86 CORRECTION COEFFICIENT DATA
90 CALIBRATION CURVE DATA
100 COMPONENT MEASUREMENT DEVICE SET
D1 TO D5 FIRST MEASURED VALUE TO FIFTH MEASURED VALUE
S CHIP ATTACHING SPACE
W1 LONG WAVELENGTH BAND
W2 SHORT WAVELENGTH BAND
W3 WAVELENGTH BAND CORRESPONDING TO FULL WIDTH AT HALF MAXIMUM
X MIXTURE
λ1 TO λ5 FIRST WAVELENGTH TO FIFTH WAVELENGTH

What is claimed is:

1. A component measurement device for measuring a component of interest in blood based on an optical property of a mixture containing a pigmentary component colored by a color reaction between the component of interest in the blood and a reagent, the component measurement device comprising:
a processor programmed to:
obtain a measured value of absorbance of the mixture at a measuring wavelength, and
estimate an absorbance of the pigmentary component, which comprises correcting the measured value of absorbance of the mixture at the measuring wavelength based on information on scattered light and a ratio between reduced hemoglobin and oxygenated hemoglobin in erythrocytes.

2. The component measurement device according to claim 1, wherein:
the processor is programmed to:
obtain a first measured value of absorbance of the mixture at a first wavelength and a second measured value of absorbance of the mixture at a second wavelength, both of which are within a wavelength band longer than the measuring wavelength within a wavelength band corresponding to a full width at half maximum of a peak wavelength band in an absorbance spectrum of the pigmentary component,
obtain a third measured value of absorbance of the mixture at a third wavelength and a fourth measured value of absorbance of the mixture at a fourth wavelength, both of which are within a wavelength band shorter than the measuring wavelength within the wavelength band corresponding to the full width at half maximum, wherein the third wavelength is a wavelength at which a difference between an absorption coefficient of the reduced hemoglobin and an absorption coefficient of the oxygenated hemoglobin is equal to or less than a first predetermined value, and the fourth wavelength is a wavelength at which the difference in the absorption coefficient is more than the first predetermined value, and
correct the measured value of absorbance of the mixture at the measuring wavelength value using the first measured value to the fourth measured value.

3. The component measurement device according to claim 2, wherein:
the third wavelength is a wavelength at which a ratio of the absorption coefficient of the oxygenated hemoglobin to the absorption coefficient of the reduced hemoglobin is equal to or more than a first predetermined threshold, and the fourth wavelength is a wavelength at which the ratio of the absorption coefficient of the oxygenated hemoglobin to the absorption coefficient of the reduced hemoglobin is less than the first predetermined threshold.

4. The component measurement device according to claim 2, wherein:
the third wavelength is a wavelength at which the absorption coefficient of the reduced hemoglobin and the absorption coefficient of the oxygenated hemoglobin are equal.

5. The component measurement device according to claim 2, wherein:
the third wavelength is in a range of 520 nm to 550 nm or in a range of 565 nm to 585 nm.

6. The component measurement device according to claim 5, wherein:
the fourth wavelength is more than 550 nm and less than 565 nm or more than 585 nm and less than 600 nm.

7. The component measurement device according to claim 2, wherein:
the first wavelength is a wavelength at which the difference between the absorption coefficient of the reduced hemoglobin and the absorption coefficient of the oxygenated hemoglobin is equal to or less than a second predetermined value, and the second wavelength is a wavelength at which the difference between the absorption coefficient of the reduced hemoglobin and the absorption coefficient of the oxygenated hemoglobin is larger than a second predetermined value.

8. The component measurement device according to claim 3, wherein:
the first wavelength is a wavelength at which the ratio of the absorption coefficient of the oxygenated hemoglobin to the absorption coefficient of the reduced hemoglobin is equal to or more than the first threshold and equal to or less than a second threshold, and the second wavelength is a wavelength at which the ratio of the absorption coefficient of the oxygenated hemoglobin to the absorption coefficient of the reduced hemoglobin is less than the first threshold or more than the second threshold.

9. The component measurement device according to claim 7, wherein:
the first wavelength is a wavelength at which the absorption coefficient of the reduced hemoglobin and the absorption coefficient of the oxygenated hemoglobin are equal.

10. The component measurement device according to claim 7, wherein:
the first wavelength is in a range of 790 nm to 810 nm.

11. The component measurement device according to claim 7, wherein:
the second wavelength is a wavelength at which the absorbance of the pigmentary component is 10% or less of the absorbance of the pigmentary component at the measuring wavelength.

12. The component measurement device according to claim 11, wherein:
the second wavelength is a wavelength at which the absorbance of the pigmentary component is 0% of the absorbance of the pigmentary component at the measuring wavelength.

13. The component measurement device according to claim 1, wherein:
the measuring wavelength is 600 nm or more and 700 nm or less.

14. A component measurement method for measuring a component of interest in blood based on an optical property of a mixture containing a pigmentary component colored by a color reaction between the component of interest in the blood and a reagent, the component measurement method comprising:
obtaining a measured value of absorbance of the mixture at a measuring wavelength; and
estimating an absorbance of the pigmentary component, which comprises correcting the measured value of absorbance of the mixture at the measuring wavelength based on information on scattered light and a ratio between reduced hemoglobin and oxygenated hemoglobin in erythrocytes.

15. A non-transient computer readable medium comprising a component measurement program for measuring a component of interest in blood based on an optical property of a mixture containing a pigmentary component colored by a color reaction between the component of interest in the blood and a reagent, the component measurement program performing steps comprising:
obtaining a measured value of absorbance of the mixture at a measuring wavelength; and
estimating an absorbance of the pigmentary component, which comprises correcting the measured value of absorbance of the mixture at the measuring wavelength based on information on scattered light and a ratio between reduced hemoglobin and oxygenated hemoglobin in erythrocytes.

16. A component measurement device configured to measure a component of interest in blood based on an optical property of a mixture containing a pigmentary component colored by a color reaction between the component of interest in the blood and a reagent, the component measurement device comprising:
a processor programmed to:
obtain a measured value of absorbance of the mixture at a measuring wavelength; and
estimate an absorbance of the pigmentary component, which comprises correcting the measured value of absorbance of the mixture at the measuring wavelength based on a ratio between reduced hemoglobin and oxygenated hemoglobin in erythrocytes.

* * * * *